US011327292B2

(12) United States Patent
Sakamoto

(10) Patent No.: US 11,327,292 B2
(45) Date of Patent: May 10, 2022

(54) METHOD OF OPERATING OBSERVATION DEVICE, OBSERVATION DEVICE, AND RECORDING MEDIUM

(71) Applicant: OLYMPUS CORPORATION, Tokyo (JP)

(72) Inventor: Yohei Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 241 days.

(21) Appl. No.: 16/821,184

(22) Filed: Mar. 17, 2020

(65) Prior Publication Data

US 2020/0301126 A1 Sep. 24, 2020

(30) Foreign Application Priority Data

Mar. 22, 2019 (JP) .............................. JP2019-054976

(51) Int. Cl.
*G02B 23/24* (2006.01)
*H04N 13/111* (2018.01)
(52) U.S. Cl.
CPC ....... *G02B 23/2484* (2013.01); *H04N 13/111* (2018.05)
(58) Field of Classification Search
None
See application file for complete search history.

(56) References Cited

U.S. PATENT DOCUMENTS

| 11,026,747 | B2* | 6/2021 | Altmann ................ A61B 6/032 |
| 2005/0182295 | A1* | 8/2005 | Soper ................ A61B 1/00172 |
| | | | 600/117 |
| 2017/0085762 | A1* | 3/2017 | Obara .................. H04N 5/2256 |
| 2017/0111600 | A1* | 4/2017 | Wang ................ G01B 11/2513 |
| 2018/0177556 | A1* | 6/2018 | Noonan ............. A61B 1/00149 |
| 2019/0175057 | A1* | 6/2019 | Krimsky ................ A61B 5/113 |
| 2019/0290111 | A1* | 9/2019 | Shademan .......... A61B 1/00165 |

FOREIGN PATENT DOCUMENTS

WO WO 2016/076262 A1 5/2016

* cited by examiner

*Primary Examiner* — Stuart D Bennett
(74) *Attorney, Agent, or Firm* — Scully, Scott, Murphy & Presser, P.C.

(57) ABSTRACT

An imaging condition set in a first region of a three-dimensional model of a subject and an imaging condition set in a second region of the three-dimensional model are different from each other. A processor of an observation device determines whether or not the imaging condition that has been set in the first region or the second region including a position on the three-dimensional model is satisfied. The position is identified on the basis of a position of an imaging device and a posture of the imaging device. The processor displays observation information on a display on the basis of a result of determination. The observation information represents whether or not the first region or the second region including the position on the three-dimensional model has been observed.

20 Claims, 22 Drawing Sheets

FIG. 6

| REGION | INDEX A (OBJECT DISTANCE) | INDEX B (OBSERVATION TIME) | INDEX C (IMAGE LUMINANCE) | INDEX D (POSITION OF VISUAL FIELD) |
|---|---|---|---|---|
| REGION R1 OF INTEREST | LESS THAN OR EQUAL TO 10 mm | BE STOPPED FOR 0.2 SEC AND OBSERVE | IMAGE LUMINANCE OF GREATER THAN OR EQUAL TO 50 AND LESS THAN 240 | FIELD ANGLE OF LESS THAN OR EQUAL TO 70 DEG |
| REGION R2 OF INTEREST | LESS THAN OR EQUAL TO 15 mm | BE STOPPED FOR 0.2 SEC AND OBSERVE | IMAGE LUMINANCE OF GREATER THAN OR EQUAL TO 50 AND LESS THAN 240 | FIELD ANGLE OF LESS THAN OR EQUAL TO 90 DEG |
| GENERAL REGION | LESS THAN OR EQUAL TO 50 mm | UNNECESSARY | IMAGE LUMINANCE OF GREATER THAN OR EQUAL TO 50 AND LESS THAN 240 | UNNECESSARY |

METHOD OF OPERATING OBSERVATION DEVICE, OBSERVATION DEVICE, AND RECORDING MEDIUM

BACKGROUND OF THE INVENTION

Field of the Invention

The present invention relates to a method of operating an observation device, an observation device, and a recording medium.

Priority is claimed on Japanese Patent Application No. 2019-054976, filed on Mar. 22, 2019, the content of which is incorporated herein by reference.

Description of Related Art

Industrial endoscope devices have been used for observation and inspection of internal damage, corrosion, and the like of boilers, turbines, engines, pipes, and the like. There is a case in which a large space such as an aircraft engine or a structure such as a pipe of long distance are subjected to inspection using an industrial endoscope device. In such inspection, it is difficult for a user to correctly understand where observation has been performed and where observation has not been performed. In many cases, a user performs inspection by using a more reliable method in order to avoid omitting observation. For this reason, there is a situation in which the same inspection region is repeatedly inspected. In this way, the efficiency of inspection decreases.

In PCT International Publication No. WO2016/076262, a method of resolving this problem is disclosed. A computer of an endoscope device determines whether or not an inspection object (subject) has been observed and notifies a user of a result of the determination. The computer determines whether or not the inspection object has been observed on the basis of an object distance of the inspection object seen in a visual field of an endoscope. If this function is provided, a user can understand where observation has been performed and where observation has not been performed, and the efficiency of inspection increases.

SUMMARY OF THE INVENTION

According to a first aspect of the present invention, a method of operating an observation device includes an image display step, an estimation step, an identification step, a determination step, and an observation information display step. The observation device includes an insertion unit, a storage medium, and a processor. The insertion unit includes an imaging device configured to acquire an image of a subject inside an observation object and is configured to be inserted into the observation object. The storage medium is configured to store an imaging condition that has been set in each of a first region and a second region. The first region is part of a three-dimensional model of the subject. The second region is other than the first region in the three-dimensional model. The imaging condition of the first region and the imaging condition of the second region are different from each other. The processor displays the image on a display in the image display step. The processor estimates, in the estimation step, a position of the imaging device and a posture of the imaging device. The position and the posture are a position and a posture, respectively, when the imaging device acquires the image. The processor identifies, in the identification step, a position on the three-dimensional model corresponding to a pixel of the image on the basis of the position and the posture that are estimated in the estimation step. The processor determines, in the determination step, whether or not the imaging condition that has been set in the first region or the second region including the position on the three-dimensional model is satisfied. The processor displays, in the observation information display step, observation information on the display on the basis of a result of the determination step. The observation information represents whether or not the first region or the second region including the position on the three-dimensional model has been observed.

According to a second aspect of the present invention, in the first aspect, the method may further include an imaging condition setting step in which the processor sets the imaging condition to each of the first region and the second region.

According to a third aspect of the present invention, in the first or second aspect, the method may further include a region setting step in which the processor sets the first region and the second region to the three-dimensional model.

According to a fourth aspect of the present invention, in the third aspect, the method may further include a feature point detection step, an association step, a calculation step, and a generation step. The processor detects a feature point in each of a plurality of images acquired by the imaging device in the feature point detection step. The processor associates the feature point between the images included in the plurality of images in the association step. The processor calculates a position of the imaging device and a posture of the imaging device on the basis of the feature point in the calculation step. The processor generates, in the generation step, the three-dimensional model on the basis of the position and the posture calculated in the calculation step. Before the region setting step is executed, the feature point detection step, the association step, the calculation step, and the generation step may be executed.

According to a fifth aspect of the present invention, in the second aspect, input of the imaging condition from a user may not be accepted in the imaging condition setting step.

According to a sixth aspect of the present invention, in the third or fourth aspect, input of information that represents the first region and the second region from a user may not be accepted in the region setting step.

According to a seventh aspect of the present invention, in any one of the first to sixth aspects, the processor may estimate the position and the posture on the basis of at least the image and the three-dimensional model in the estimation step.

According to an eighth aspect of the present invention, in any one of the first to sixth aspects, the processor may estimate the position and the posture on the basis of only the image in the estimation step.

According to a ninth aspect of the present invention, in any one of the first to eighth aspects, the storage medium may be configured to store a non-observed position that is the position on the three-dimensional model for which it is determined that the imaging condition is not satisfied. The method may further include a first notification information display step in which, when the non-observed position is behind a visual field of the imaging device, the processor displays first notification information that represents that there is the first region or the second region including the non-observed position on the display.

According to a tenth aspect of the present invention, in any one of the first to ninth aspects, the imaging condition may include a plurality of conditions. The method may further include a condition information display step in which, when the processor determines that at least one condition included in the plurality of conditions is not satisfied, the processor displays condition information that represents the at least one condition on the display.

According to an eleventh aspect of the present invention, in any one of the first to tenth aspects, the method may further include a recording step in which, when the processor determines that the imaging condition that has been set to the first region is satisfied, the processor records the image in which a region corresponding to the first region is seen.

According to a twelfth aspect of the present invention, in any one of the first to eleventh aspects, when the processor determines that the imaging condition is satisfied, the processor may display, in the observation information display step, the observation information representing that the first region or the second region including the position on the three-dimensional model has been observed on the display.

According to a thirteenth aspect of the present invention, in any one of the first to twelfth aspects, when the processor determines that the imaging condition is not satisfied, the processor may display, in the observation information display step, the observation information representing that the first region or the second region including the position on the three-dimensional model has not been observed on the display.

According to a fourteenth aspect of the present invention, in any one of the first to eleventh aspects, the processor may calculate, in the determination step, an evaluation value that represents a degree to which the imaging condition that has been set in the first region or the second region is satisfied. The processor may display the evaluation value as the observation information on the display in the observation information display step.

According to a fifteenth aspect of the present invention, in the fourteenth aspect, the processor may determine whether or not the imaging condition is satisfied by comparing the evaluation value with a threshold value in the determination step. The method may further include a second notification information display step in which, when the processor determines that the imaging condition is not satisfied, the processor displays second notification information that represents the first region or the second region including the position on the three-dimensional model has not been observed on the display.

According to a sixteenth aspect of the present invention, an observation device includes an insertion unit, a storage medium, and a processor. The insertion unit includes an imaging device configured to acquire an image of a subject inside an observation object and is configured to be inserted into the observation object. The storage medium is configured to store an imaging condition that has been set in each of a first region and a second region. The first region is part of a three-dimensional model of the subject. The second region is other than the first region in the three-dimensional model. The imaging condition of the first region and the imaging condition of the second region are different from each other. The processor is configured to display the image on a display. The processor is configured to estimate a position of the imaging device and a posture of the imaging device. The position and the posture are a position and a posture, respectively, when the imaging device acquires the image. The processor is configured to identify a position on the three-dimensional model corresponding to a pixel of the image on the basis of the estimated position and the posture. The processor is configured to determine whether or not the imaging condition that has been set in the first region or the second region including the position on the three-dimensional model is satisfied. The processor is configured to display observation information on the display on the basis of a result of determination of the imaging condition. The observation information represents whether or not the first region or the second region including the position on the three-dimensional model has been observed.

According to a seventeenth aspect of the present invention, a non-transitory computer-readable recording medium saves a program for causing a computer to execute an image display step, an estimation step, an identification step, a determination step, and an observation information display step. The observation device includes an insertion unit and a storage medium. The insertion unit includes an imaging device configured to acquire an image of a subject inside an observation object and is configured to be inserted into the observation object. The storage medium is configured to store an imaging condition that has been set in each of a first region and a second region. The first region is part of a three-dimensional model of the subject. The second region is other than the first region in the three-dimensional model. The imaging condition of the first region and the imaging condition of the second region are different from each other. The computer displays the image on a display in the image display step. The computer estimates, in the estimation step, a position of the imaging device and a posture of the imaging device. The position and the posture are a position and a posture, respectively, when the imaging device acquires the image. The computer identifies, in the identification step, a position on the three-dimensional model corresponding to a pixel of the image on the basis of the position and the posture estimated in the estimation step. The computer determines, in the determination step, whether or not the imaging condition that has been set in the first region or the second region including the position on the three-dimensional model is satisfied. The computer displays, in the observation information display step, observation information on the display on the basis of a result of the determination step, the observation information representing whether or not the first region or the second region including the position on the three-dimensional model has been observed.

According to an eighteenth aspect of the present invention, in the seventeenth aspect, the program may cause the computer to further execute a region setting step in which the computer sets the first region and the second region to the three-dimensional model.

According to a nineteenth aspect of the present invention, in the seventeenth aspect, the program may cause the computer to further execute a feature point detection step, an association step, a calculation step, and a generation step. The computer detects a feature point in each of a plurality of images acquired by the imaging device in the feature point detection step. The computer associates the feature point between the images included in the plurality of images in the association step. The computer calculates a position of the imaging device and a posture of the imaging device on the basis of the feature point in the calculation step. The computer generates the three-dimensional model on the basis of the position and the posture calculated in the calculation step in the generation step. Before the region setting step is executed, the feature point detection step, the association step, the calculation step, and the generation step may be executed.

According to a twentieth aspect of the present invention, in the seventeenth aspect, the computer may estimate the position and the posture on the basis of at least the image and the three-dimensional model in the estimation step.

BRIEF DESCRIPTION OF THE DRAWINGS

FIG. 6 is a diagram showing an index of determination and a threshold value of determination in the first embodiment of the present invention.

DETAILED DESCRIPTION OF THE INVENTION

Hereinafter, embodiments of the present invention will be described with reference to the drawings. Hereinafter, an example in which an observation device is an endoscope device will be described. The observation device has only to be a device including an insertion unit to be inserted into an observation object and acquiring an image of a subject in the observation object. The observation device is not limited to an endoscope device.

First Embodiment

Figure 1:
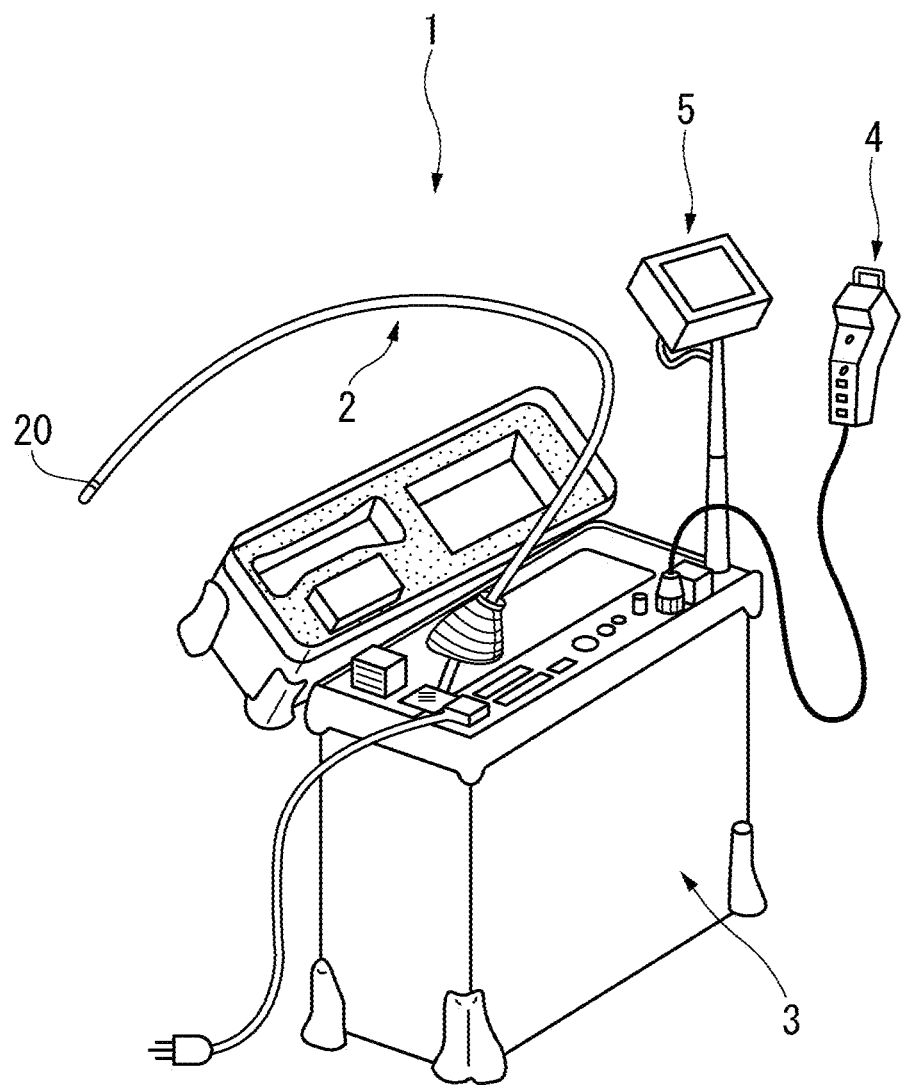
FIG. 1 is a perspective view showing an entire configuration of an endoscope device according to a first embodiment of the present invention.
Figure 2:
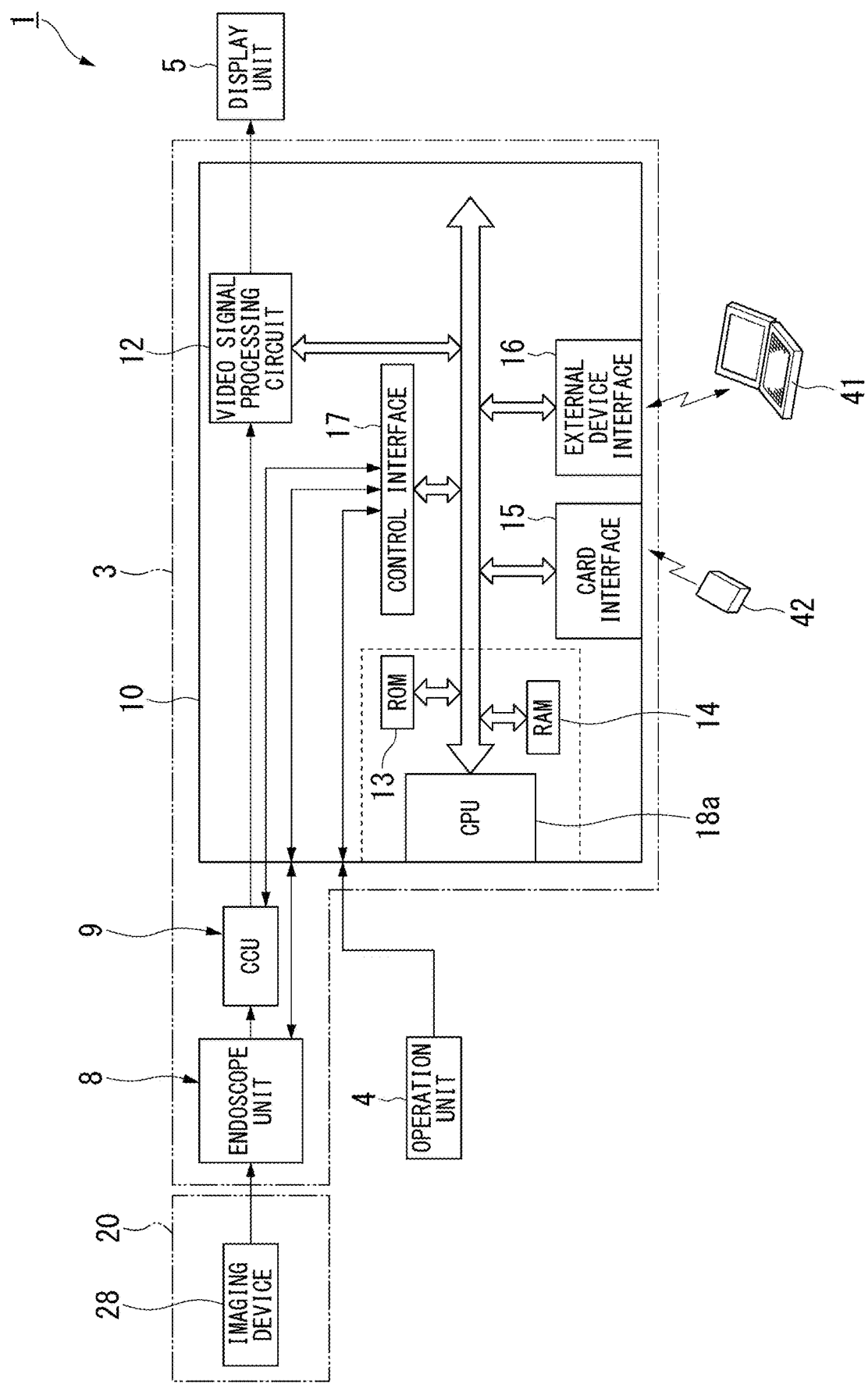
FIG. 2 is a block diagram showing an internal configuration of the endoscope device according to the first embodiment of the present invention.

FIG. 1 shows an entire configuration of an endoscope device 1 according to a first embodiment of the present invention. FIG. 2 shows an internal configuration of the endoscope device 1. The endoscope device 1 images a subject and generates an image. In order to observe various subjects, an inspector can perform replacement of an optical adaptor mounted at a tip end of an insertion unit 2, selection of a built-in video processing program, and addition of a video processing program. Hereinafter, a case in which a user designates a region of interest prior to inspection will be described. A region of interest is defined as an inspection region for which a condition for determining whether or not the inspection region has been observed is different from the condition of other inspection regions.

The endoscope device 1 shown in FIG. 1 includes the insertion unit 2, a main body unit 3, an operation unit 4, and a display unit 5.

The insertion unit 2 is inserted into the inside of a subject. The insertion unit 2 has a long and thin bendable tube shape from the tip end 20 to a base end portion. The insertion unit 2 images a subject and outputs an imaging signal to the main body unit 3. An optical adapter is mounted on the tip end 20 of the insertion unit 2. For example, a single-eye optical adapter is mounted on the tip end 20 of the insertion unit 2. The main body unit 3 is a control device including a housing unit that houses the insertion unit 2. The operation unit 4 accepts a user's operation for the endoscope device 1. The display unit 5 includes a display screen and displays an image of a subject acquired by the insertion unit 2, an operation menu, and the like on the display screen.

The operation unit 4 is a user interface. For example, the operation unit 4 is at least one of a button, a switch, a key, a mouse, a joystick, a touch pad, a track ball, and a touch panel. The display unit 5 is a monitor (display) such as a liquid crystal display (LCD). The display unit 5 may be a touch panel. In such a case, the operation unit 4 and the display unit 5 are integrated.

The main body unit 3 shown in FIG. 2 includes an endoscope unit 8, a camera control unit (CCU) 9, and a control device 10. The endoscope unit 8 includes a light source device and a bending device not shown in the drawing. The light source device supplies illumination light that is necessary for observation. The bending device bends a bending mechanism that is built into the insertion unit 2. An imaging device 28 is built into the tip end 20 of the insertion unit 2. The imaging device 28 is an image sensor. The imaging device 28 photo-electrically converts an optical image of a subject formed by an optical adaptor and generates an imaging signal. The CCU 9 drives the imaging device 28. An imaging signal output from the imaging device 28 is input to the CCU 9. The CCU 9 executes a pre-process including amplification, noise elimination, and the like for the imaging signal acquired by the imaging device 28. The CCU 9 converts the imaging signal for which the pre-process has been executed into a video signal such as an NTSC signal.

The control device 10 includes a video signal processing circuit 12, a read only memory (ROM) 13, a random access memory (RAM) 14, a card interface 15, an external device interface 16, a control interface 17, and a central processing unit (CPU) 18*a*.

The video signal processing circuit 12 performs predetermined video processing on the video signal output from the CCU 9. For example, the video signal processing circuit 12 performs video processing related to improvement of visibility. For example, the video processing is color reproduction, gray scale correction, noise suppression, contour enhancement, and the like. For example, the video signal processing circuit 12 combines the video signal output from the CCU 9 and a graphic image signal generated by the CPU 18*a*. The graphic image signal includes an image of the operation screen and the like. The video signal processing circuit 12 outputs a combined video signal to the display unit 5.

The ROM 13 is a nonvolatile recording medium on which a program for the CPU 18*a* to control the operation of the endoscope device 1 is recorded. The RAM 14 is a volatile recording medium that temporarily stores information used by the CPU 18*a* for controlling the endoscope device 1. The CPU 18*a* controls the operation of the endoscope device 1 on the basis of a program recorded on the ROM 13.

A memory card 42 that is a removable recording medium is connected to the card interface 15. The card interface 15 inputs control processing information, image information, and the like stored in the memory card 42 to the control device 10. In addition, the card interface 15 records the control processing information, the image information, and the like generated by the endoscope device 1 on the memory card 42.

An external device such as a USB device is connected to the external device interface 16. For example, a personal computer (PC) 41 is connected to the external device interface 16. The external device interface 16 transmits information to the PC 41 and receives information from the PC 41. Accordingly, a monitor of the PC 41 can display information. In addition, by inputting an instruction to the PC 41, a user can perform an operation related to control of the endoscope device 1.

The control interface 17 performs communication with the operation unit 4, the endoscope unit 8, and the CCU 9 for operation control. The control interface 17 notifies the CPU 18*a* of an instruction input to the operation unit 4 by a user. The control interface 17 outputs control signals used for controlling the light source device and the bending device to the endoscope unit 8. The control interface 17 outputs a control signal used for controlling the imaging device 28 to the CCU 9.

A program executed by the CPU 18*a* may be recorded on a computer-readable recording medium. The program recorded on this recording medium may be read and executed by a computer other than the endoscope device 1. For example, the PC 41 may read and execute the program. The PC 41 may control the endoscope device 1 by transmitting control information used for controlling the endoscope device 1 to the endoscope device 1 in accordance with a program. Alternatively, the PC 41 may acquire a video signal from the endoscope device 1 and may process the acquired video signal.

The program described above may be transmitted from the computer storing the program to the endoscope device 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). A combination of a program that has already been recorded in a computer and a differential program may realize the functions described above.

The above-described endoscope device 1 includes the insertion unit 2, the RAM 14, and the CPU 18*a*. The insertion unit 2 includes the imaging device 28 and is inserted into an inspection object (observation object). The imaging device 28 images a subject in the inspection object and generates an imaging signal. In this way, the imaging device 28 generates an image (image data) of the subject on the basis of an optical image of the subject in an imaging visual field. The imaging device 28 generates an inspection moving image of the subject by continuously generating a plurality of images. The image generated by the imaging device 28 is input to the CPU 18*a* through the video signal processing circuit 12. The RAM 14 (storage medium) stores an imaging condition that has been set in each of a region of interest (first region) that is part of a three-dimensional (3D) model of the subject and a general region (second region) other than the region of interest in the 3D model. The imaging condition is used for determining whether or not a region of the subject has been observed. The imaging condition of the region of interest and the imaging condition of the general region are different from each other. Hereinafter, an example in which the PC 41 performs setting of a region and setting of an imaging condition will be described.

Figure 3:
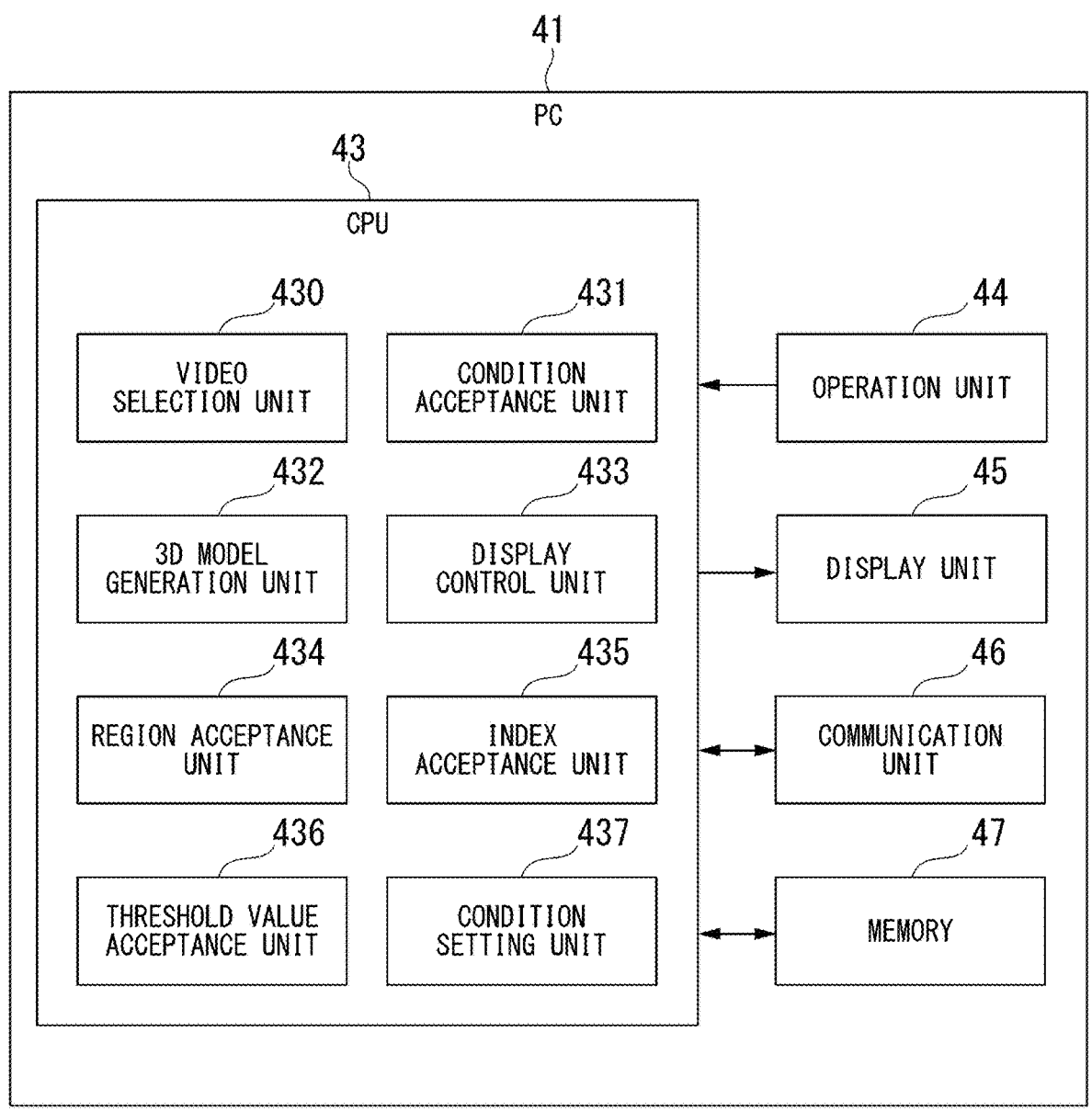
FIG. 3 is a block diagram showing a functional configuration of a PC according to the first embodiment of the present invention.

FIG. 3 shows a functional configuration of the PC 41. The PC 41 shown in FIG. 3 includes a CPU 43, an operation unit 44, a display unit 45, a communication unit 46, and a memory 47.

The CPU 43 controls an operation of the PC 41. The operation unit 44 is a user interface. The operation unit 44 accepts a user's operation for the PC 41. A user can input various kinds of information to the PC 41 by operating the operation unit 44. The operation unit 44 accepts information input by a user and outputs the information to the CPU 43. The display unit 45 includes a display screen and displays a 3D model of a subject in an inspection object and the like on the display screen. The display unit 45 is a monitor (display) such as an LCD. The display unit 45 may be a touch panel. In such a case, the operation unit 44 and the display unit 45 are integrated. The communication unit 46 performs communication with the endoscope device 1. The memory 47 stores an inspection moving image acquired by the endoscope device 1 and the like.

The functions of the CPU 43 are constituted by a video selection unit 430, a condition acceptance unit 431, a 3D model generation unit 432, a display control unit 433, a region acceptance unit 434, an index acceptance unit 435, a threshold value acceptance unit 436, and a condition setting unit 437. At least one of the blocks in the CPU 43 shown in FIG. 3 may be constituted by a circuit different from the CPU 43.

Each unit in the CPU 43 may be constituted by at least one of a processor and a logic circuit. For example, the processor is at least one of a CPU, a digital signal processor (DSP), and a graphics processing unit (GPU). For example, the logic circuit is at least one of an application specific integrated circuit (ASIC) and a field-programmable gate array (FPGA). Each unit in the CPU 43 may include one or a plurality of processors. Each unit in the CPU 43 may include one or a plurality of logic circuits.

The communication unit 46 receives a plurality of inspection moving images from the endoscope device 1. The memory 47 stores the received plurality of inspection moving images. A user inputs information that represents an inspection moving image to be used for setting a region of interest and setting an imaging condition to the operation unit 44. The video selection unit 430 selects one of the plurality of inspection moving images on the basis of the information input to the operation unit 44 by a user. The memory 47 may store only one inspection moving image and the video selection unit 430 may select the inspection moving image. Hereinafter, an example in which a moving image of a subject is used for setting a region of interest and setting an imaging condition will be described. A moving image is not necessarily used and a still image may be used.

A user inputs information that represents a condition for generating a 3D model of a subject to the operation unit 44. The condition acceptance unit 431 accepts the condition for generating the 3D model of the subject on the basis of the information input to the operation unit 44 by a user. Specifically, the condition includes an internal parameter of a camera, a distortion correction parameter of the camera, a setting value, a reference length, and the like. The setting value is used for a variety of pieces of processing for generating a 3D model. The reference length is used for matching the 3D model with the actual scale of a subject. The information accepted by the condition acceptance unit 431 is stored on the memory 47.

The 3D model generation unit 432 (processing unit) generates (reconfigures) a 3D model of a subject. The 3D model generated by the 3D model generation unit 432 is stored on the memory 47.

The display control unit 433 displays the 3D model generated by the 3D model generation unit 432 on the display unit 45.

A user inputs information that represents a region of interest on a subject to the operation unit 44. The region acceptance unit 434 (region setting unit) accepts the region of interest on the basis of the information input to the operation unit 44 by a user. A region that is not designated as a region of interest by a user is accepted as a general region. The region acceptance unit 434 sets the region of interest and the general region to the 3D model generated by the 3D model generation unit 432. Each region accepted by the region acceptance unit 434 is stored on the memory 47.

A user inputs information that represents an index for determining whether or not a region on a subject has been observed to the operation unit 44. The index represents a type of an imaging condition. It is possible for a user to designate an index for each region. The index acceptance unit 435 accepts an index on the basis of the information input to the operation unit 44 by a user. The index accepted by the index acceptance unit 435 is stored on the memory 47.

A user inputs information that represents a threshold value for determining whether or not a region on a subject has been observed to the operation unit 44. It is possible for a user to designate a threshold value for each region. The threshold value acceptance unit 436 accepts a threshold value on the basis of the information input to the operation unit 44 by a user. The threshold value accepted by the threshold value acceptance unit 436 is stored on the memory 47.

The condition setting unit 437 (imaging condition setting unit) sets an imaging condition including an index and a threshold value to each of the region of interest and the general region of the 3D model generated by the 3D model generation unit 432. The condition setting unit 437 sets an index of the region of interest and a threshold value of the region of interest to the region of interest. The condition setting unit 437 sets an index of the general region and a threshold value of the general region to the general region. The condition setting unit 437 generates a 3D model to which an imaging condition of each region has been set. The 3D model includes data of three-dimensional coordinates of a subject, information of the region of interest, information of the general region, and the imaging condition of each region. The 3D model generated by the condition setting unit 437 is stored on the memory 47. The communication unit 46 transmits the 3D model to which the imaging condition has been set to the endoscope device 1.

The external device interface 16 of the endoscope device 1 transmits the inspection moving image acquired by the imaging device 28 to the PC 41. The external device interface 16 receives the 3D model to which the imaging condition has been set from the PC 41. The 3D model is stored on the RAM 14.

Figure 4:
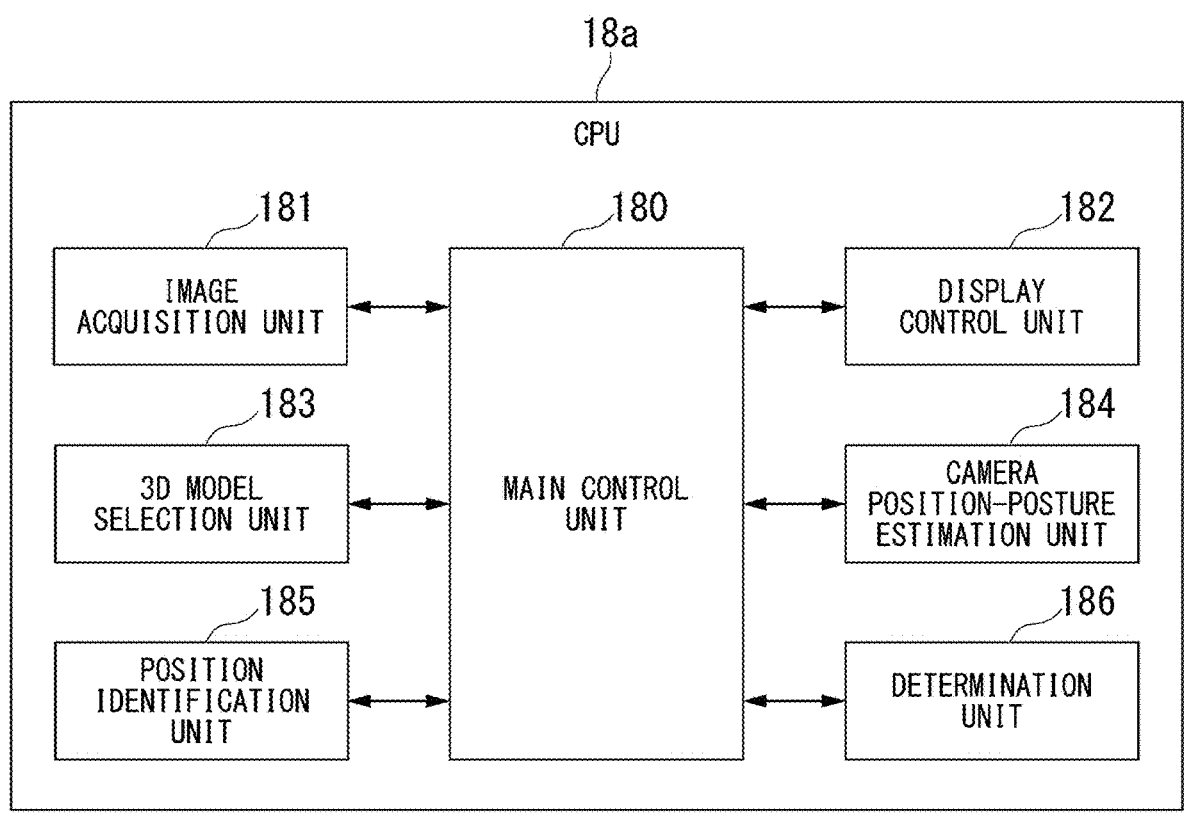
FIG. 4 is a block diagram showing a functional configuration of a CPU according to the first embodiment of the present invention.

FIG. 4 shows a functional configuration of the CPU 18*a*. The functions of the CPU 18*a* are constituted by a main control unit 180, an image acquisition unit 181, a display control unit 182, a 3D model selection unit 183, a camera position-posture estimation unit 184, a position identification unit 185, and a determination unit 186. At least one of the blocks shown in FIG. 4 may be constituted by a circuit other than the CPU 18*a*.

Each unit shown in FIG. 4 may be constituted by at least one of a processor and a logic circuit. Each unit shown in FIG. 4 may include one or a plurality of processors. Each unit shown in FIG. 4 may include one or a plurality of logic circuits.

The main control unit 180 controls processing executed by each unit. The image acquisition unit 181 acquires an image generated by the imaging device 28 from the video signal processing circuit 12. The acquired image is held on the RAM 14.

The display control unit 182 displays the image generated by the imaging device 28 on the display unit 5. For example, the display control unit 182 controls the processing executed by the video signal processing circuit 12. The display control unit 182 causes the video signal processing circuit 12 to output the processed image to the display unit 5. The display unit 5 displays the image output from the video signal processing circuit 12.

The display control unit 182 displays a 3D model, a determination result, and the like on the display unit 5. In other words, the display control unit 182 displays various kinds of information on an image. For example, the display control unit 182 generates a graphic image signal of various kinds of information. The display control unit 182 outputs the generated graphic image signal to the video signal processing circuit 12. The video signal processing circuit 12 combines a video signal output from the CCU 9 and the graphic image signal output from the CPU 18a. In this way, various kinds of information are superimposed on an image. The video signal processing circuit 12 outputs the combined video signal to the display unit 5. The display unit 5 displays an image on which various kinds of information are superimposed on the basis of the video signal.

A user inputs information that represents a 3D model of a subject to the operation unit 4. The operation unit 4 accepts the information input to the operation unit 4 by a user and outputs the information. The information input to the operation unit 4 is input to the control interface 17 that is an input unit. The information input to the control interface 17 is input to the CPU 18a. The 3D model selection unit 183 selects a 3D model on the basis of the information input to the operation unit 4 by a user.

The camera position-posture estimation unit 184 estimates the position of the imaging device 28 and the posture of the imaging device 28. The estimated position and posture are a position of the imaging device 28 and a posture of the imaging device 28, respectively, when the imaging device 28 acquires an image. The camera position-posture estimation unit 184 uses the image acquired by the image acquisition unit 181 and the 3D model selected by the 3D model selection unit 183 in order to estimate the position of the imaging device 28 and the posture of the imaging device 28.

The position identification unit 185 identifies a position on the 3D model corresponding to a pixel of the image acquired by the image acquisition unit 181. The position identification unit 185 uses the image acquired by the image acquisition unit 181, the 3D model selected by the 3D model selection unit 183, and the position and the posture estimated by the camera position-posture estimation unit 184 in order to identify a position on the 3D model.

The determination unit 186 determines whether or not the imaging condition that has been set to the region of interest or the general region including the position identified by the position identification unit 185 is satisfied. Specifically, the determination unit 186 acquires the index and the threshold value that has been set to the position identified by the position identification unit 185. The determination unit 186 calculates an index value on the basis of the image acquired by the image acquisition unit 181 and the position and the posture estimated by the camera position-posture estimation unit 184. The determination unit 186 determines whether or not the imaging condition is satisfied by comparing the calculated index value with the threshold value.

The display control unit 182 displays observation information on the display unit 5 on the basis of a result of the determination performed by the determination unit 186. The observation information represents whether or not the region of interest or the general region including the position identified by the position identification unit 185 has been observed. The display control unit 182 generates a graphic image signal of the observation information. Thereafter, processing similar to the processing for displaying various kinds of information is executed.

Characteristic processing of the first embodiment includes processing executed prior to inspection and processing executed during inspection. Hereinafter, each of the pieces of processing will be described. Hereinafter, an image generated by the imaging device 28 for inspection is described as an inspection image.

Figure 5:
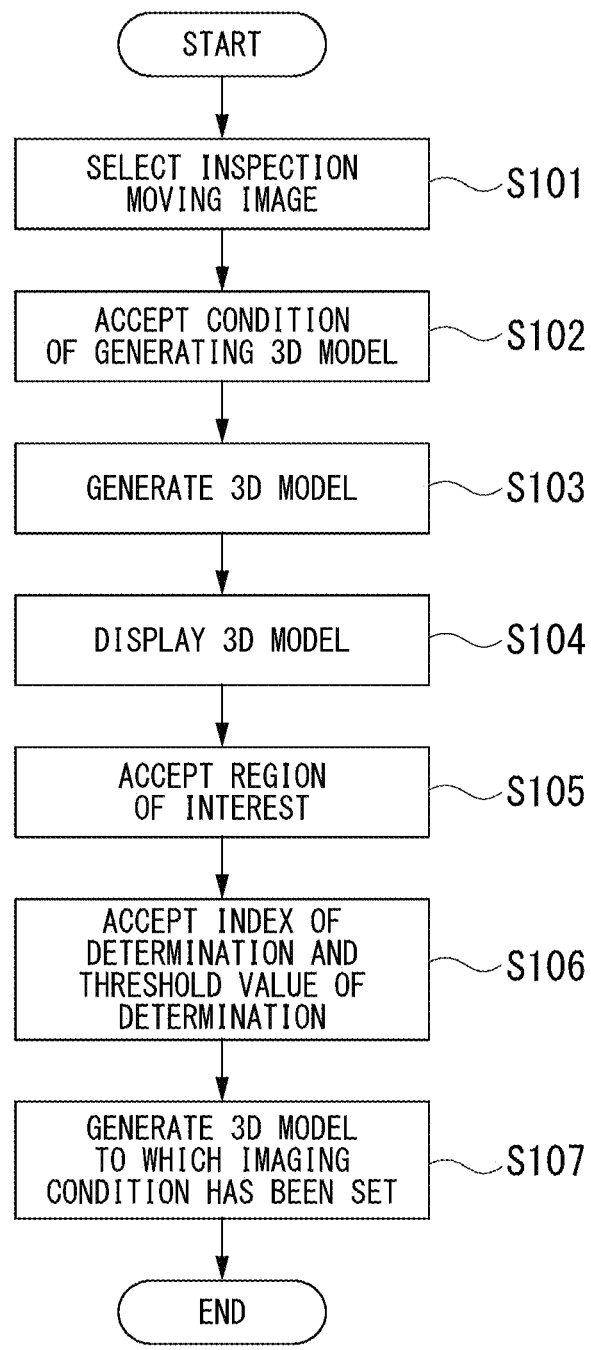
FIG. 5 is a flow chart showing a procedure of processing executed by the PC according to the first embodiment of the present invention.

A procedure of processing executed prior to inspection will be described with reference to FIG. 5. FIG. 5 shows a procedure of processing executed by the PC 41. The PC 41 may be any of a desktop and a laptop. In addition, the processing shown in FIG. 5 may be executed in a cloud environment.

A user inputs information that represents an inspection moving image used for setting a region of interest and setting an imaging condition to the operation unit 44. The video selection unit 430 selects one of a plurality of inspection moving images on the basis of the information input to the operation unit 44 by a user (Step S101).

After Step S101, a user inputs information that represents a condition for generating a 3D model of a subject to the operation unit 44. The condition acceptance unit 431 accepts the condition for generating the 3D model of the subject on the basis of the information input to the operation unit 44 by a user (Step S102). As described above, the condition includes an internal parameter of a camera, a distortion correction parameter of the camera, a setting value, a reference length, and the like. A user does not need to designate all of these conditions. The CPU 43 may automatically set at least one of these conditions.

After Step S102, the 3D model generation unit 432 generates a 3D model of a subject on the basis of the selected inspection moving image and the condition for generating the 3D model (Step S103). A procedure of specific processing executed by the 3D model generation unit 432 will be described later.

After Step S103, the display control unit 433 displays the generated 3D model on the display unit 45 (Step S104).

After Step S104, a user determines a region to be designated as a region of interest in the 3D model and inputs information that represents the region to the operation unit 44. The region acceptance unit 434 accepts the region of interest on the basis of the information input to the operation unit 44 by a user. The region acceptance unit 434 sets the region of interest and a general region to the generated 3D model (Step S105).

For example, a user designates a region in which the degree of importance of inspection is high as a region of interest. A region of interest may be a region in which defects were frequently found in the past inspection. A region of interest may be a region for which it was determined that follow-up observation was necessary in the past inspection. A region of interest may be a region in which a flaw is likely to occur due to a design.

A region of interest may be a region in which the degree of importance is not especially high. For example, a region of interest may be a region required to be inspected under a specific condition. The specific condition is an object distance, composition of an image, or a type of an optical adaptor. A region of interest may be set on the basis of an inspection manual or design intention of an inspection object. For example, in inspection of aircraft engines, design intention is shared between an engine manufacturer and an inspection department of each business in many cases.

In the first embodiment, a user designates a region of interest on a 3D model while the 3D model is displayed on the display unit 45. A user does not need to directly designate a region on a 3D model as a region of interest. A user may designate a region on a two-dimensional subject seen in an inspection moving image as a region of interest. Specifically, in Step S104, an inspection moving image is displayed on the display unit 45 instead of a 3D model. A user determines a region to be designated as a region of interest in a two-dimensional subject and inputs information that represents the region to the operation unit 44. The region acceptance unit 434 accepts the region of interest on the basis of the information input to the operation unit 44 by a user. A position on a 3D model and a position on a two-dimensional subject are associated with each other. Therefore, it is possible for the CPU 43 to identify a region on a 3D model corresponding to a region designated on a two-dimensional subject.

After Step S105, a user inputs information that represents an index of determination and a threshold value of determination to the operation unit 44. The index acceptance unit 435 accepts the index on the basis of the information input to the operation unit 44 by a user. The threshold value acceptance unit 436 accepts the threshold value on the basis of the information input to the operation unit 44 by a user (Step S106). The index and the threshold value are accepted for each region. In other words, the index and the threshold value of the region of interest are accepted and the index and the threshold value of the general region are accepted.

FIG. 6 shows an example of an index of determination and a threshold value of determination. Four indices are shown in FIG. 6. The four indices include an index A (object distance), an index B (observation time), an index C (image luminance), and an index D (position within a visual field). The index A represents the distance from a subject to the tip end of the endoscope. The index B represents a length of time in which the tip end of the endoscope is stopped for observation. The index C represents a luminance value of an inspection image. The index D represents a field angle from the center of an image to the position of each region. Each of the indices shown in FIG. 6 is calculated on the basis of an inspection image. A threshold value of each index in each of two regions of interest and one general region are shown in FIG. 6. The two regions of interest are a region R1 of interest and a region R2 of interest.

In the example shown in FIG. 6, all of the four indices are set to the two regions of interest. In the example shown in FIG. 6, only the index A and the index C are set to the general region.

An index set in each region is not limited to the example shown in FIG. 6. For example, the index B may not be included. An index E that is not shown in FIG. 6 may be added. At least one index has only to be set. An index may be the reliability of three-dimensional coordinates calculated on the basis of an inspection image. An index may be a relative posture (observation angle) of the tip end of the endoscope with respect to a subject. An index may be a type of an optical adaptor used for inspection.

A threshold value set to each region is not limited to the example shown in FIG. 6. A threshold value may be changed in accordance with an endoscope equipment or a subject. A threshold value may be changed in accordance with the proficiency of a user for inspection.

Figure 7:
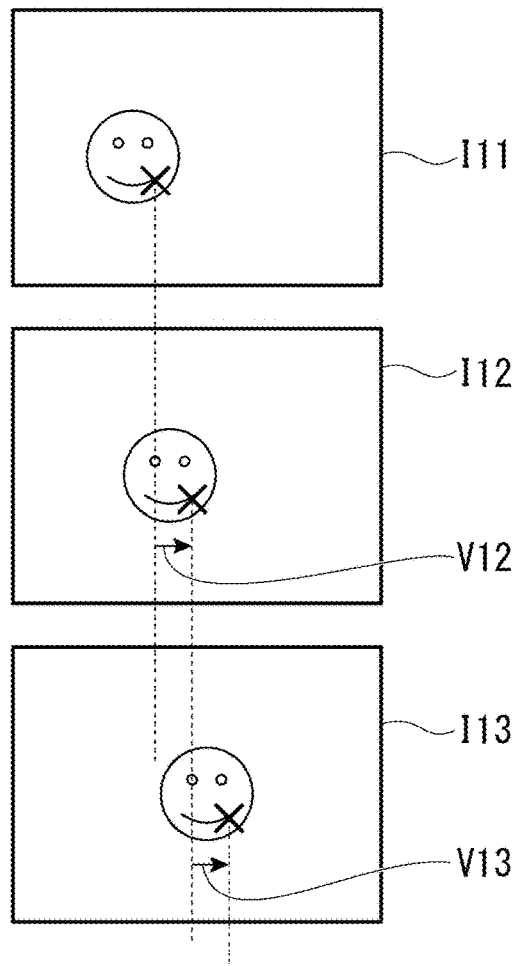
FIG. 7 is a diagram showing an inspection image and a motion vector in the first embodiment of the present invention.

Specific determination processing using the index B will be described with reference to FIG. 7 and FIG. 8. Three inspection images I11 to I13 shown in FIG. 7 are defined as described below. The inspection image I11 (reference image) is an image acquired at a first time point by the image acquisition unit 181. The inspection image I12 is an image acquired at a second time point following the first time point by the image acquisition unit 181. The inspection image I13 is an image acquired at a third time point following the second time point by the image acquisition unit 181.

The determination unit 186 detects a representative point seen in the inspection image I11. The determination unit 186 detects a motion vector V12 of the representative point on the basis of the inspection image I11 and the inspection image I12. Similarly, the determination unit 186 detects a motion vector V13 of the representative point on the basis of the inspection image I12 and the inspection image I13.

Figure 8:
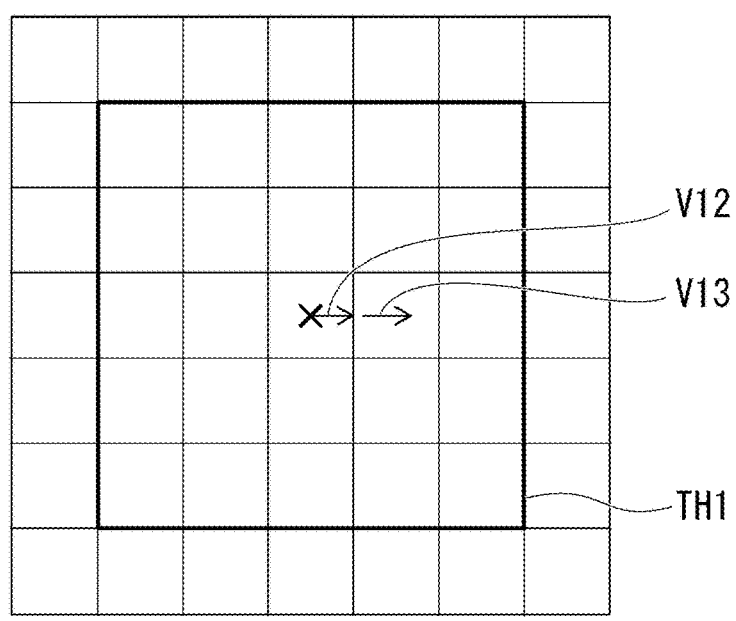
FIG. 8 is a diagram showing the relationship between a motion vector and a threshold value in the first embodiment of the present invention.

FIG. 8 shows the relationship between each motion vector and a threshold value. A threshold value TH1 is an allowable value of motion determined in advance. In this example, the determination unit 186 calculates the sum of motion vectors between timings at which respective inspection images of these three frames are acquired. If the sum does not exceed the threshold value TH1, the determination unit 186 determines that a subject has been inspected in a stationary state. In this example, the sum (maximum distance) of motion vectors between respective inspection images is set as the threshold value. A value that is allowable as the amount of motion between respective inspection images may be set as the threshold value. In other words, the determination unit 186 may determine whether or not the amount of motion between respective inspection images in a period set in advance is less than or equal to the threshold value.

In a case in which the motion of a camera is translational motion, the amount of motion in an inspection image varies for each object distance. For this reason, after the index A (object distance) is satisfied, the determination unit 186 may determine the value of the index B (observation time).

After Step S106, the condition setting unit 437 sets an imaging condition of each of the region of interest and the general region to the generated 3D model. In this way, the condition setting unit 437 generates a 3D model to which the imaging condition has been set (Step S107). When Step S107 is executed, the processing shown in FIG. 5 is completed.

After the processing shown in FIG. 5 is completed, the communication unit 46 transmits the 3D model to which the imaging condition has been set to the endoscope device 1. The external device interface 16 of the endoscope device 1 receives the 3D model from the PC 41. The received 3D model is stored on the RAM 14.

A procedure of specific processing executed by the 3D model generation unit 432 will be described. The 3D model generation unit 432 uses the inspection moving image selected by the video selection unit 430 and the condition accepted by the condition acceptance unit 431. Hereinafter, an example in which the 3D model generation unit 432 uses two inspection images extracted from the inspection moving image will be described. When a camera captures two inspection images, two viewpoints of the camera are different from each other. Even when three or more inspection images are used, a basic principle is not changed from that of the case in which two inspection images are used. A method described below may be applied also to a case in which three or more inspection images are used.

Figure 9:
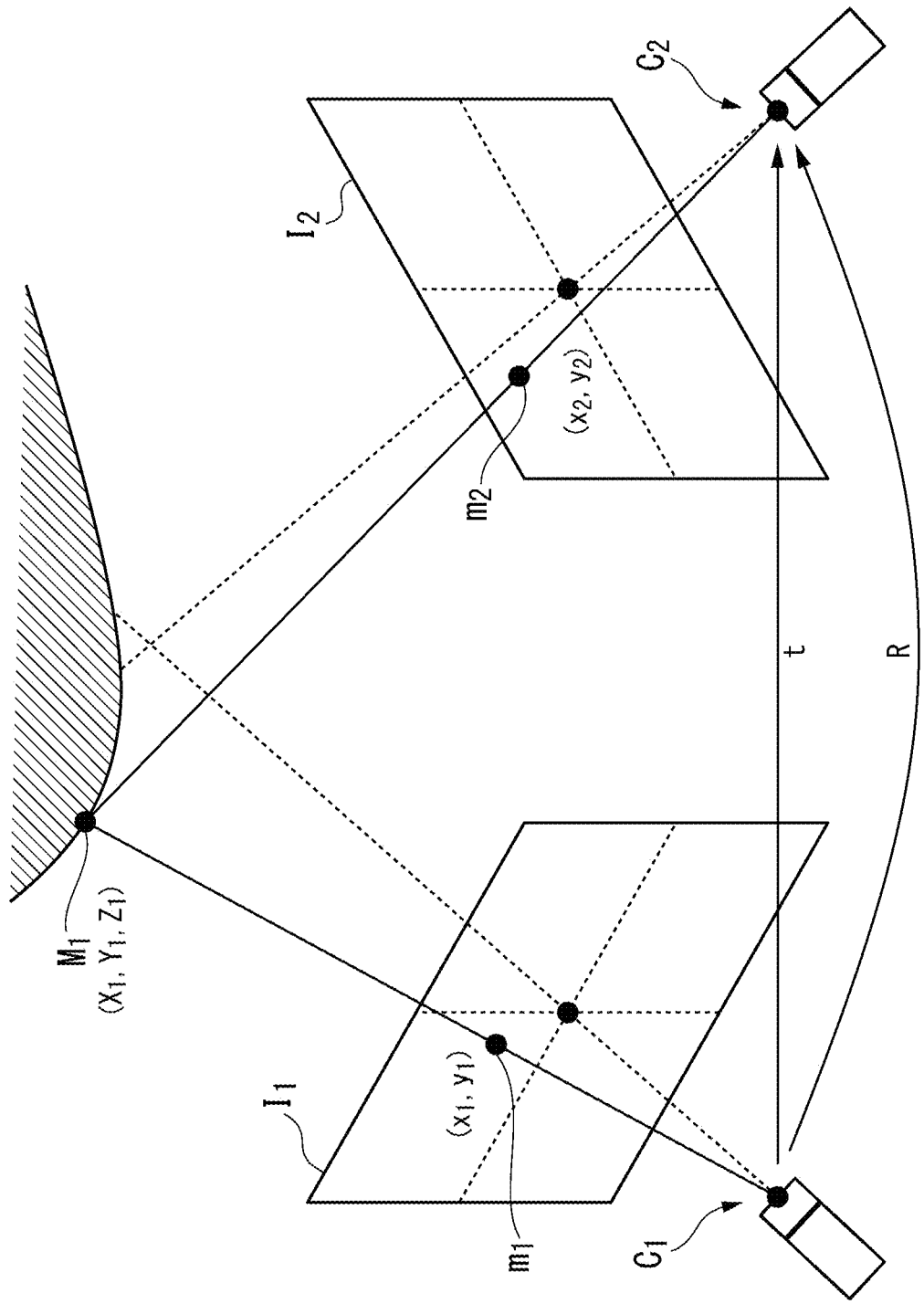
FIG. 9 is a schematic diagram showing a situation in which an image is acquired in the first embodiment of the present invention.

FIG. 9 schematically shows a status of image acquisition in a case in which two inspection images of a subject are acquired. In the description described below, an expression "camera" in a broad sense is used. The camera in the description described below specifically indicates an observation optical system of the tip end of the endoscope (the tip end 20 of the insertion unit 2).

As shown in FIG. 9, first, an inspection image $I_1$ is acquired in an imaging state $c_1$ of the camera. Next, an inspection image $I_2$ is acquired in an imaging state $c_2$ of the camera. At least one of an imaging position and an imaging posture is different between the imaging state $c_1$ and the imaging state $c_2$. In FIG. 9, both the imaging position and the imaging posture are different between the imaging state $c_1$ and the imaging state $c_2$.

In each embodiment of the present invention, it is assumed that the inspection image $I_1$ and the inspection image $I_2$ are acquired by the same endoscope. In addition, in each embodiment of the present invention, it is assumed that parameters of an objective optical system of the endoscope do not change. The parameters of the objective optical system are a focal distance, a distortion aberration, a pixel size of an image sensor, and the like. Hereinafter, for the convenience of description, the parameters of the objective optical system will be abbreviated to internal parameters. When such conditions are assumed, the internal parameters describing characteristics of the optical system of the endoscope can be used in common regardless of the position and the posture of the tip end of the endoscope. In each embodiment of the present invention, it is assumed that the internal parameters are acquired at the time of factory shipment. In addition, it is assumed that the internal parameters are known at the time of acquiring an inspection image.

In each embodiment of the present invention, it is assumed that two or more inspection images are extracted from the inspection moving image and the inspection moving image is acquired by one endoscope. However, the present invention is not limited to this. For example, the present invention may be applied to also a case in which a 3D model is restored by using a plurality of inspection moving images acquired by a plurality of endoscopes. In this case, the inspection image $I_1$ and the inspection image $I_2$ have only to be acquired by using different endoscopes and each internal parameter has only to be stored for each endoscope. Even if the internal parameters are unknown, it is possible to perform calculation by using the internal parameters as variables. For this reason, the subsequent procedure does not greatly change in accordance with whether or not the internal parameters are known.

Figure 10:
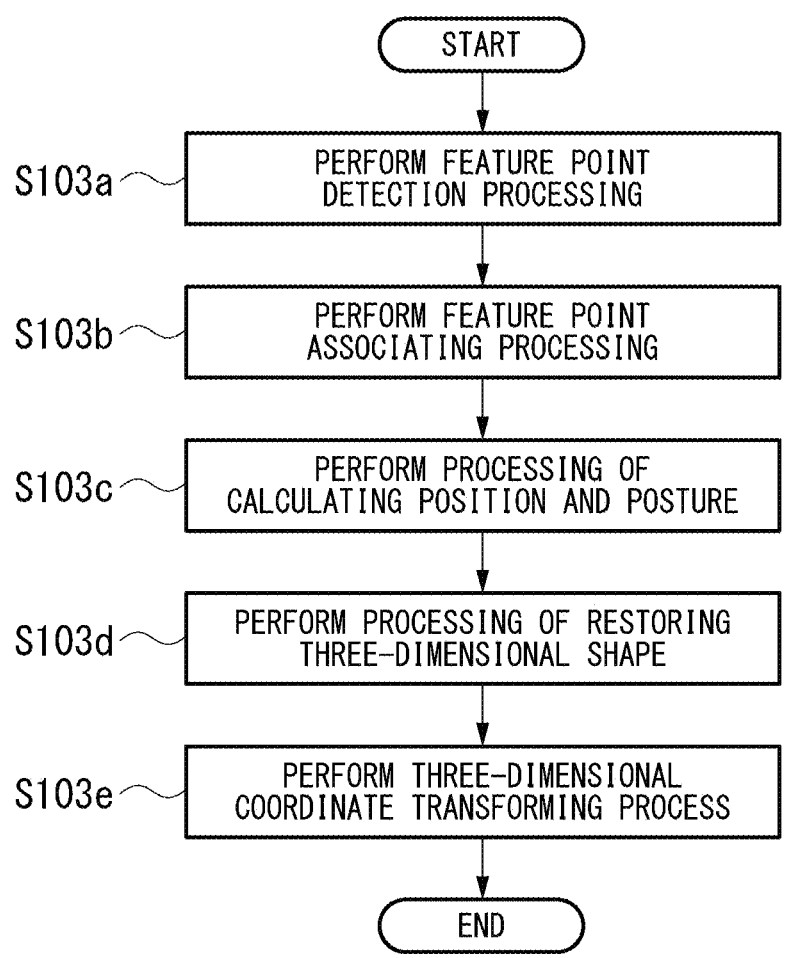
FIG. 10 is a flow chart showing a procedure of processing for generating a three-dimensional model in the first embodiment of the present invention.

A procedure for calculating three-dimensional coordinates of a subject on the basis of acquired two inspection images will be described with reference to FIG. 10. FIG. 10 shows the procedure of processing for generating a 3D model.

First, the 3D model generation unit 432 executes a feature point detection processing (Step S103a). The 3D model generation unit 432 detects a feature point of each of acquired two inspection images in the feature point detection processing. The feature point represents a corner, an edge, and the like in which an image luminance gradient is large in information of a subject seen in the inspection image. As a method of detecting this feature point, a scale-invariant feature transform (SIFT), a feature from accelerated segment test (FAST), or the like is used. By using such a method, a feature point within an image can be detected.

FIG. 9 shows an example in which a feature point $m_1$ is detected from the inspection image $I_1$ and a feature point $m_2$ is detected from the inspection image $I_2$. Although only one feature point of each image is shown in FIG. 9, in fact, a plurality of feature points are detected in each image. There is a possibility that the number of feature points detected in each image is different. Each feature point detected from each image is converted into data called a feature quantity. The feature quantity is data that represent a feature of a feature point.

After Step S103a, the 3D model generation unit 432 executes a feature point associating processing (Step S103b). In the feature point associating processing, the 3D model generation unit 432 compares correlations of feature quantities between inspection images for each feature point detected in the feature point detection processing (Step S103a). In a case in which the correlations of the feature quantities are compared and a feature point of which feature quantities are close to those of a feature point of another inspection image is found in each inspection image, the 3D model generation unit 432 stores the information on the RAM 14. In this way, the 3D model generation unit 432 associates a feature point of each inspection image together. On the other hand, in a case in which a feature point of which feature quantities are close to those of a feature point of another inspection image is not found, the 3D model generation unit 432 discards information of the feature point.

After Step S103b, the 3D model generation unit 432 reads coordinates of feature points of two inspection images associated with each other (a feature point pair) from the RAM 14. The 3D model generation unit 432 executes processing of calculating a position and a posture on the basis of the read coordinates (Step S103c). In the processing of calculating a position and a posture, the 3D model generation unit 432 calculates a relative position and a relative posture between the imaging state $c_1$ of the camera that has acquired the inspection image $I_1$ and the imaging state $c_2$ of the camera that has acquired the inspection image $I_2$. More specifically, the 3D model generation unit 432 calculates a matrix E by solving the following Equation (1) using an epipolar restriction.

$$p_1^T E p_2 = 0 \quad E = [t]_X R \quad \because [t]_X = \begin{pmatrix} 0 & -t_z & t_y \\ t_z & 0 & -t_x \\ -t_y & t_x & 0 \end{pmatrix} \quad (1)$$

The matrix E is called a basic matrix. The basic matrix E is a matrix storing a relative position and a relative posture between the imaging state $c_1$ of the camera that has acquired the inspection image $I_1$ and the imaging state $c_2$ of the camera that has acquired the inspection image $I_2$. In Equation (1), a matrix $p_1$ is a matrix including coordinates of a feature point detected from the inspection image $I_1$. A matrix $p_2$ is a matrix including coordinates of a feature point detected from the inspection image $I_2$. The basic matrix E includes information related to a relative position and a relative posture of the camera and thus corresponds to external parameters of the camera. The basic matrix E can be solved by using a known algorithm.

As shown in FIG. 9, Expression (2) and Expression (3) are satisfied in a case in which the amount of position change of the camera is t and the amount of posture change of the camera is R.

$$t = (t_x, t_y, t_z) \quad (2)$$

$$R = R_x(\alpha)R_y(\beta)R_z(\gamma) \quad (3)$$

$$= \begin{pmatrix} 1 & 0 & 0 \\ 0 & \cos\alpha & -\sin\alpha \\ 0 & \sin\alpha & \cos\alpha \end{pmatrix} \begin{pmatrix} \cos\beta & 0 & \sin\beta \\ 0 & 1 & 0 \\ -\sin\beta & 0 & \cos\beta \end{pmatrix}$$

$$\begin{pmatrix} \cos\gamma & -\sin\gamma & 0 \\ \sin\gamma & \cos\gamma & 0 \\ 0 & 0 & 1 \end{pmatrix}$$

In Expression (2), the amount of movement in an x-axis direction is expressed as $t_x$, the amount of movement in a y-axis direction is expressed as $t_y$, and the amount of movement in a z-axis direction is expressed as $t_z$. In Expression (3), a rotation amount α around the x-axis is expressed as $R_x(\alpha)$, a rotation amount β around the y axis is expressed as $R_y(\beta)$, and a rotation amount γ around the z axis is expressed as $R_z(\gamma)$. After the basic matrix E is calculated, optimization processing called bundle adjustment may be executed in order to improve restoration accuracy of three-dimensional coordinates.

After Step S103c, the 3D model generation unit 432 executes processing of restoring a three-dimensional shape of a subject on the basis of the relative position and the relative posture of the camera (the amount of position change t and the amount of posture change R) calculated in Step S103c (Step S103d). The 3D model generation unit 432 generates a 3D model of a subject in the processing of restoring a three-dimensional shape. As a technique for restoring a three-dimensional shape of a subject, there is matching processing that uses patch-based multi-view stereo (PMVS) and parallelization stereo and the like. However, a means therefor is not particularly limited.

After Step S103d, the 3D model generation unit 432 executes a three-dimensional coordinate transforming processing on the basis of the three-dimensional shape data of a subject calculated in the processing of restoring a three-dimensional shape (Step S103d) and the reference length accepted by the condition acceptance unit 431 (Step S103e). The 3D model generation unit 432 transforms the three-dimensional shape data of a subject into three-dimensional coordinate data having a dimension of a length in the three-dimensional coordinate transforming processing. When Step S103e is executed, the processing shown in FIG. 10 is completed.

Figure 11:
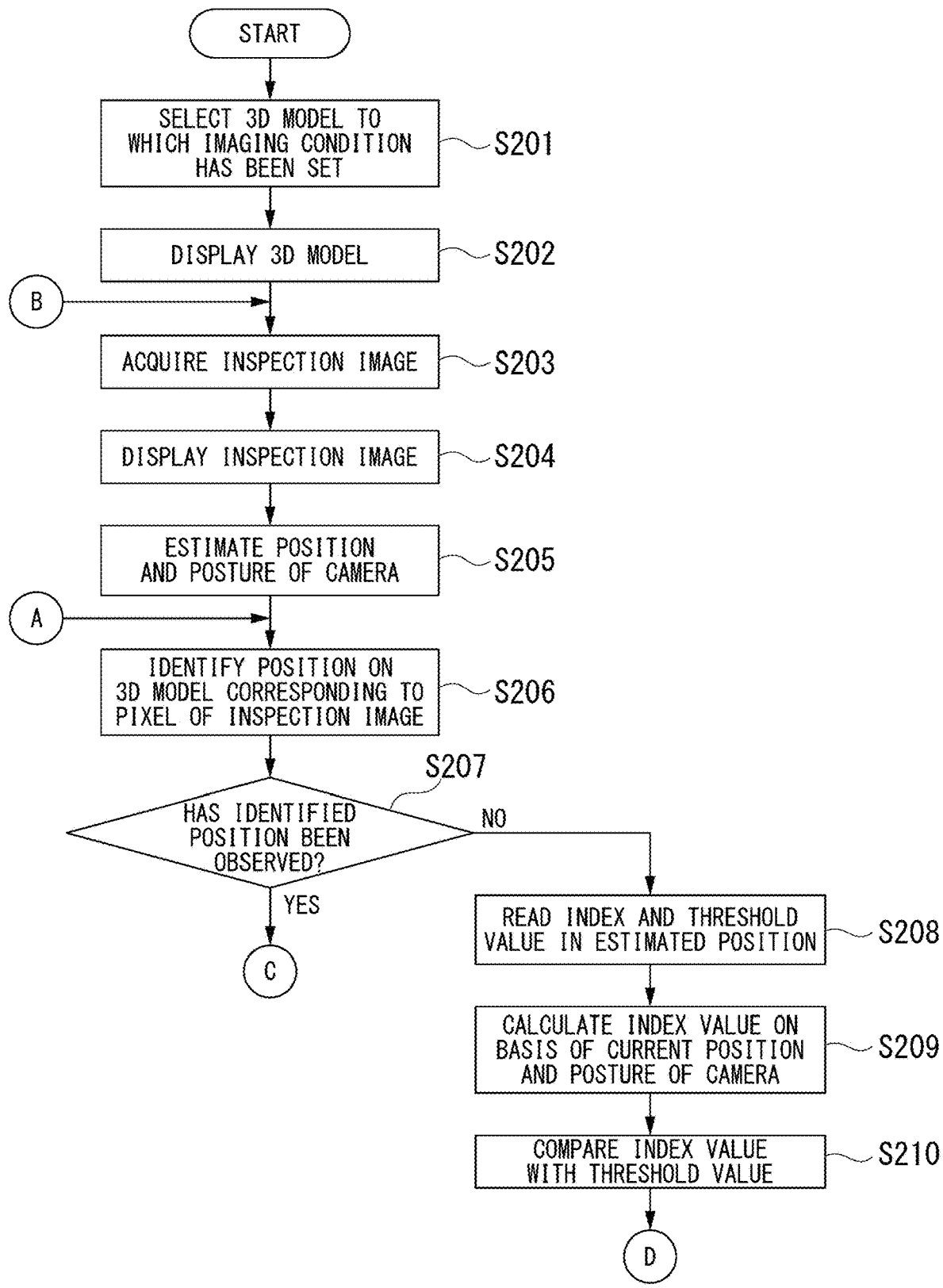
FIG. 11 is a flow chart showing a procedure of processing executed by the CPU according to the first embodiment of the present invention.
Figure 12:
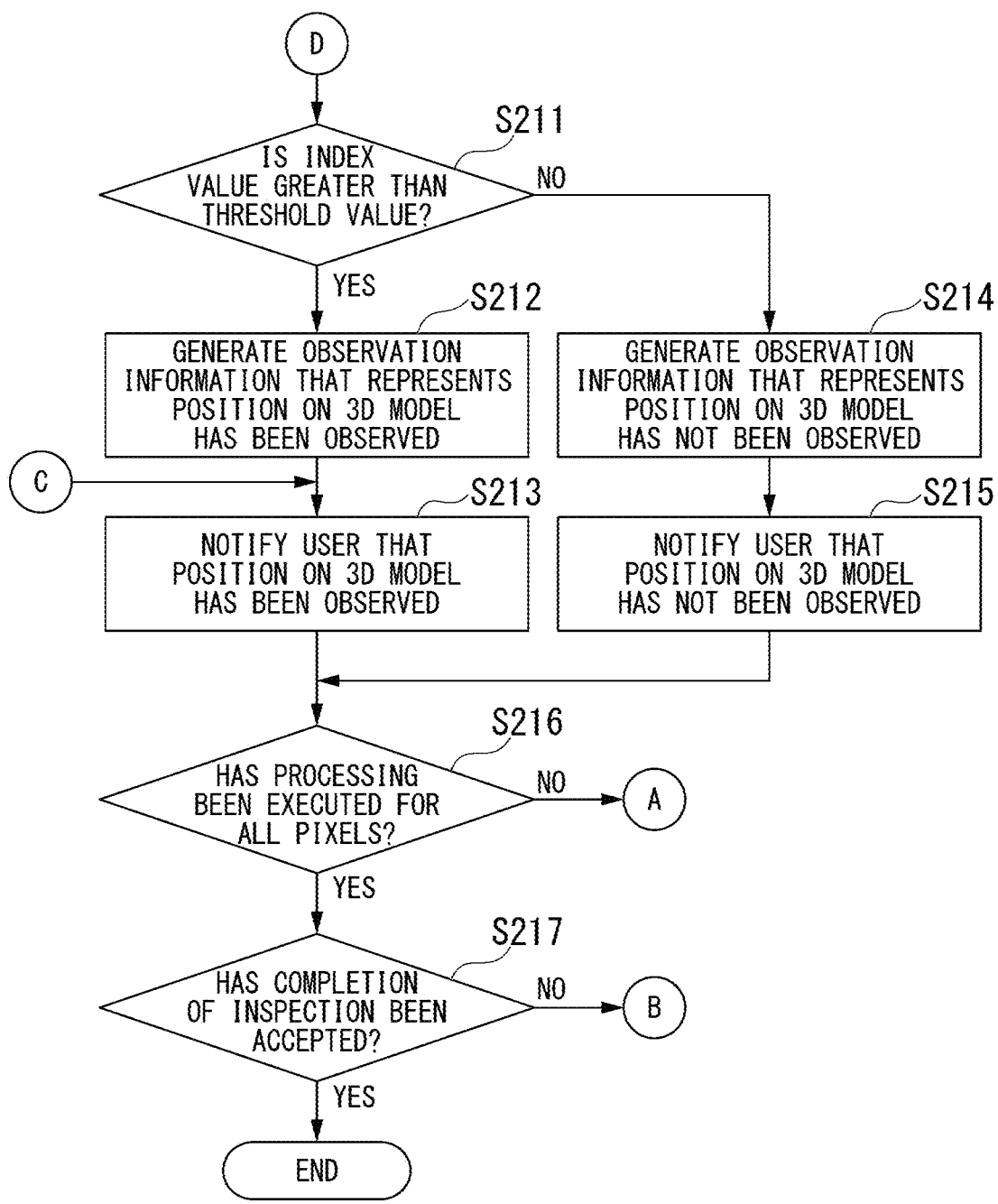
FIG. 12 is a flow chart showing a procedure of processing executed by the CPU according to the first embodiment of the present invention.

A procedure of processing executed during inspection will be described with reference to FIG. 11 and FIG. 12. FIG. 11 and FIG. 12 show a procedure of processing executed by the CPU 18a.

After the power of the endoscope device 1 is supplied, the insertion unit 2 is inserted into an inspection object and inspection is started. After the inspection is started, a user inputs information that represents a 3D model of a subject to the operation unit 4. The operation unit 4 accepts the information input to the operation unit 4 by a user. The 3D model selection unit 183 selects a 3D model stored on the RAM 14 on the basis of the information input to the operation unit 4 by a user. The 3D model selection unit 183 reads the selected 3D model from the RAM 14 (Step S201).

After Step S201, the display control unit 182 generates a graphic image signal for displaying the 3D model selected by the 3D model selection unit 183 and outputs the graphic image signal to the video signal processing circuit 12. The video signal processing circuit 12 combines the graphic image signal and a video signal and outputs the combined video signal to the display unit 5. The video signal includes color data of each pixel in an image of the 3D model. Each pixel is associated with three-dimensional coordinates. The display unit 5 displays an image of the 3D model on the basis of the video signal (Step S202).

Figure 13:
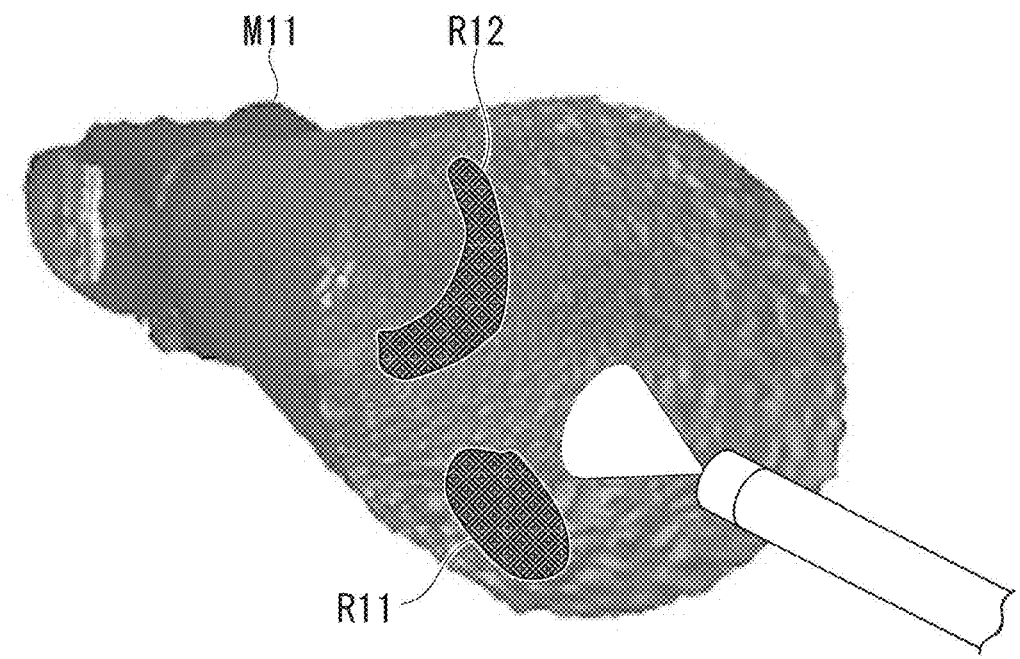
FIG. 13 is a diagram showing an example of an image displayed on a display unit according to the first embodiment of the present invention.

FIG. 13 shows an example of an image displayed on the display unit 5 in Step S202. A 3D model M11 is displayed on the display unit 5. A region R11 of interest and a region R12 of interest are displayed on the 3D model M11. A general region is a region on the 3D model M11 excluding the region R11 of interest and the region R12 of interest. For example, the region R11 of interest and the region R12 of interest are displayed in a predetermined color. The region R11 of interest and the region R12 of interest may be translucently displayed such that a user can visually recognize the 3D model M11. For example, the region R11 of interest corresponds to the region R1 of interest in FIG. 6 and the region R12 of interest corresponds to the region R2 of interest in FIG. 6. As long as a user can distinguish between the region of interest and the general region, any display method may be used.

After Step S202, the image acquisition unit 181 acquires an inspection image from the video signal processing circuit 12 (Step S203). After Step S203, the display control unit 182 displays the acquired inspection image on the display unit 5 (Step S204).

A region of interest may be displayed on the inspection image. In a case in which a small region of interest such as a cooling hole of an aircraft engine is far away from a camera, there is a possibility that a user does not notice a region of interest on a 3D model or an inspection image. In order to surely notify a user of the position of the region of interest, the display control unit 182 may display the region of interest larger than its original size.

Figure 14:
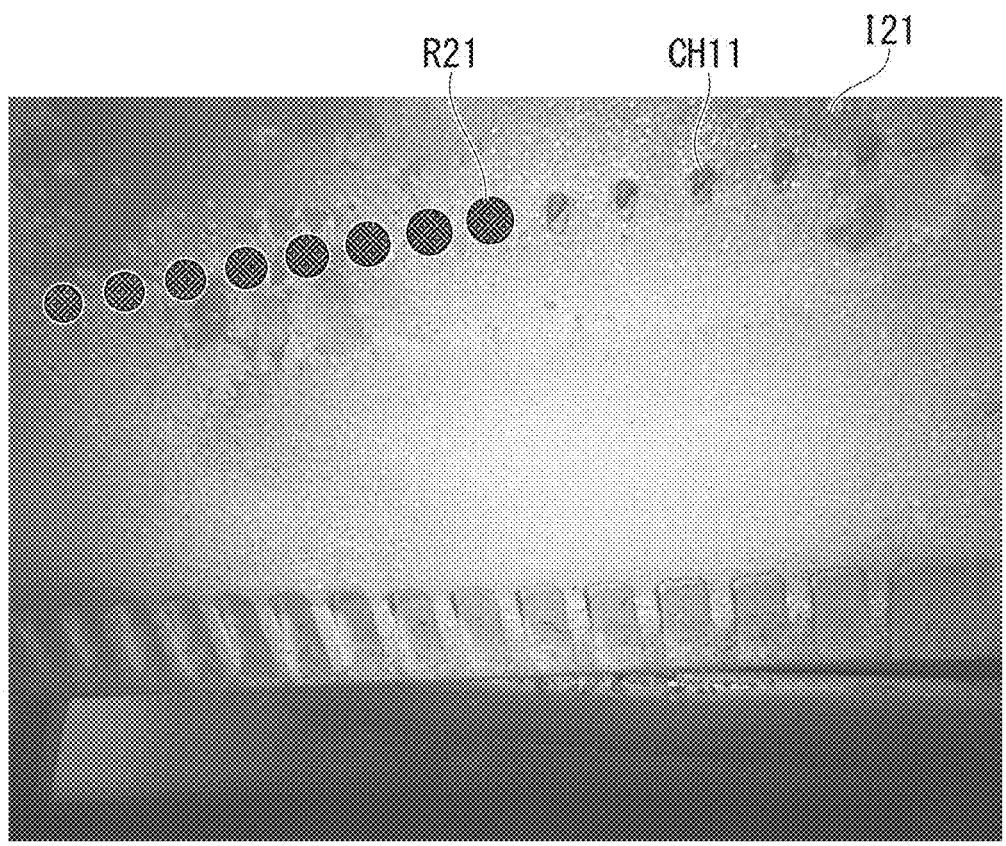
FIG. 14 is a diagram showing an example of an image displayed on the display unit according to the first embodiment of the present invention.

FIG. 14 shows an example of an inspection image displayed on the display unit 5 in Step S204. An inspection image $I_{21}$ is displayed on the display unit 5 and a plurality of regions R21 of interest are displayed on the inspection image $I_{21}$. The region R21 of interest includes a cooling hole CH11. The region R21 of interest is set larger than the cooling hole CH11. In order to make FIG. 14 easier to understand, the regions R21 of interest corresponding to only some of a plurality of cooling holes CH11 are shown.

After Step S204, the camera position-posture estimation unit 184 estimates the position and the posture of a camera when the camera acquires an inspection image on the basis of at least one inspection image and the 3D model (Step S205). The processing for estimating the position and the posture of a camera is generally called a perspective-n-point problem (PnP problem). By solving the PnP problem using a known technique (for example, open source software or the like), it is possible to estimate the position and the posture of a camera.

The present invention is not limited to a method of estimating the position and the posture of a camera by solving the PnP problem. For example, the camera position-posture estimation unit 184 may estimate the position and the posture of a camera by using a sensor incorporated in a scope unit of the endoscope. The sensor is an acceleration sensor, a gyro sensor, a magnetic sensor, or the like. In addition, the camera position-posture estimation unit 184 may estimate the position and the posture of a camera by combining a variety of sensors to improve the accuracy of solving the PnP problem and shorten processing time. Therefore, the camera position-posture estimation unit 184 may estimate the position and the posture of a camera on the basis of at least the inspection image and the 3D model.

In the example described below, it is assumed that the camera position-posture estimation unit 184 estimates the position and the posture of a camera by solving the PnP problem without using a sensor. The camera position-posture estimation unit 184 estimates the position and the posture of a camera on the basis of only the inspection image.

After Step S205, the position identification unit 185 identifies a position on the 3D model corresponding to a pixel of the inspection image (Step S206). The pixel subjected to be processed in Step S206 is a pixel for which each piece of processing after Step S206 has not been executed yet.

Figure 15:
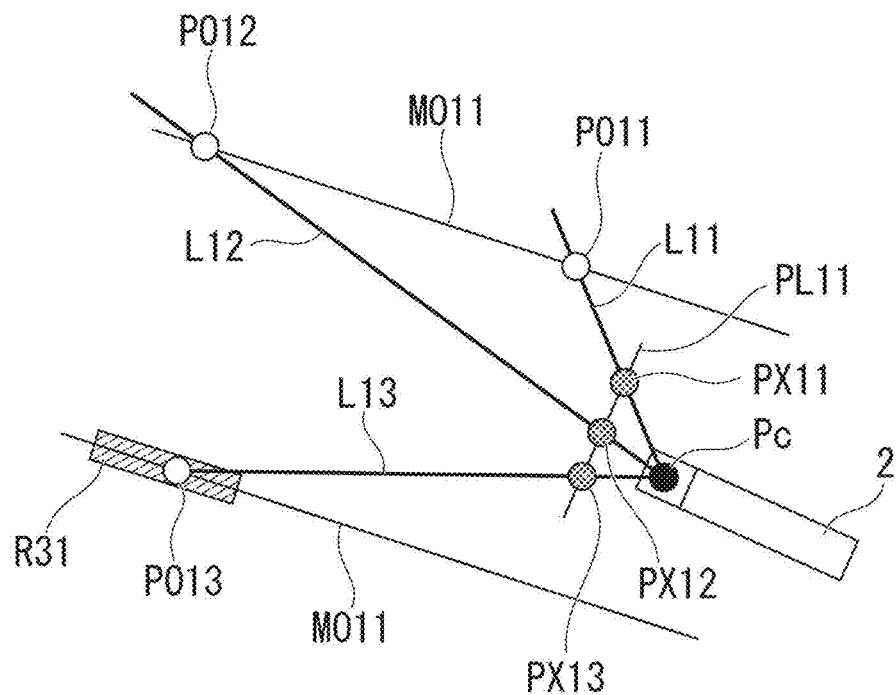
FIG. 15 is a diagram showing a method of identifying a position on a three-dimensional model in the first embodiment of the present invention.

Details of Step S206 will be described with reference to FIG. 15. FIG. 15 shows a method of identifying a position on the 3D model. A 3D model MO11 has a tube shape. A cross section passing through the center axis of the 3D model MO11 is shown in FIG. 15. A state in which the insertion unit 2 is virtually inserted into the 3D model MO11 is shown in FIG. 15.

In Step S206, a position Pc of a camera with respect to the 3D model MO11 is estimated. A region R31 of interest is set on the 3D model MO11. For example, the region R31 of interest corresponds to the region R1 of interest in FIG. 6. A plane PL11 is a virtual image plane on a perspective projection model. The plane PL11 is calculated on the basis of the position Pc and the posture of the camera estimated in Step S206. The position of the plane PL11 corresponds to a pixel of an inspection image. Hereinafter, the position of the plane PL11 is called a pixel.

A straight line that passes through the position Pc and each pixel can be defined. Hereinafter, this straight line is called a visual line. A visual line L11 passes through the position Pc and a pixel PX11. A visual line L12 passes through the position Pc and a pixel PX12. A visual line L13 passes through the position Pc and a pixel PX13. After each visual line is calculated, it is possible to calculate an intersection point of each visual line and the 3D model MO11. A position PO11 is an intersection point of the visual line L11 and the 3D model MO11. A position PO12 is an intersection point of the visual line L12 and the 3D model MO11. A position PO13 is an intersection point of the visual line L13 and the 3D model MO11. Each of the position PO11, the position PO12, and the position PO13 is a point on the inner wall of the 3D model MO11. It is possible for the position identification unit 185 to identify a position on the 3D model MO11 corresponding to coordinates (subject information) on an inspection image by calculating the position PO11 and the like.

After Step S206, the determination unit 186 determines whether or not predetermined information has been set at the position identified in Step S206. In this way, the determination unit 186 determines whether or not the position identified in Step S206 has been observed (Step S207). The predetermined information represents that a position on the 3D model has been observed.

In Step S211 described later, it is determined whether or not a position on the 3D model has been observed. When it is determined that a position on the 3D model has been observed, information that represents that the position has been observed is set to the position in Step S212. The determination unit 186 determines whether or not the information has been set to a position on the 3D model in Step S207. When the information has been set to a position on the 3D model, the determination unit 186 determines that the position has been observed. When the information has not been set to a position on the 3D model, the determination unit 186 determines that the position has not been observed.

When the determination unit 186 determines that the position identified in Step S206 has been observed, Step S213 is executed. When the determination unit 186 determines that the position identified in Step S206 has not been observed, the determination unit 186 reads an index and a threshold value at the position from the RAM 14 (Step S208). For example, when the position PO13 is identified in Step S206, the determination unit 186 reads an index and a threshold value that has been set to the position PO13 from the RAM 14. The position PO13 is included in the region R31 of interest corresponding to the region R1 of interest in FIG. 6. For this reason, the determination unit 186 reads an index and a threshold value that has been set to the region R1 of interest from the RAM 14. The position PO11 and the position PO12 are included in a general region. When the position PO11 or the position PO12 is identified in Step S206, the determination unit 186 reads an index and a threshold value that has been set to the general region in FIG. 6 from the RAM 14.

After Step S208, the determination unit 186 calculates an index value at the position identified in Step S206 (Step S209). Specifically, the determination unit 186 calculates an index value by using the inspection image, the position of the camera, the posture of the camera, and the 3D model. The determination unit 186 calculates a specific value of the index read in Step S208.

For example, the determination unit 186 calculates a value of the index A (object distance) shown in FIG. 6 on the basis of the position of the camera, the posture of the camera, and the 3D model. For example, the determination unit 186 calculates a value of the object distance at the position PO11 by calculating the distance between the position Pc and the position PO11 on the 3D model MO11 shown in FIG. 15. The determination unit 186 calculates a value of each of the index B (stoppage time), the index C (image luminance), and the index D (position within a visual field) on the basis of the inspection image.

The position PO13 shown in FIG. 15 is included in the region R1 of interest shown in FIG. 6. When the position PO13 is identified in Step S206, the determination unit 186 calculates a value of each of the four indices shown in FIG. 6. The position PO11 and the position PO12 shown in FIG. 15 are included in a general region. When the position PO11 or the position PO12 is identified in Step S206, the determination unit 186 calculates only a value of each of the index A and the index C shown in FIG. 6.

After Step S209, the determination unit 186 compares the index value calculated in Step S209 with the threshold value read in Step S208 (Step S210).

After Step S210, the determination unit 186 determines whether or not the index value is greater than the threshold value. In this way, the determination unit 186 determines whether or not the position identified in Step S206 has been observed (Step S211). When a plurality of index values are calculated in Step S209, the determination unit 186 compares each index value with the threshold value in Step S210. Further, the determination unit 186 determines in Step S211 as follows. When all of the plurality of index values are greater than the threshold value, the determination unit 186 determines that the index value is greater than the threshold value. When at least one of the plurality of index values is less than or equal to the threshold value, the determination unit 186 determines that the index value is not greater than the threshold value.

When only one of the plurality of index values is greater than the threshold value, the determination unit 186 may determine that the index value is greater than the threshold value. A method of determination in Step S211 is not limited to the above-described method. The determination unit 186 may perform the above-described determination on the basis of the logical product or the logical sum of a determination result obtained by comparing each index value with the threshold value, or on the basis of a combination of the logical product and the logical sum.

When the determination unit 186 determines that the index value is greater than the threshold value, the determination unit 186 generates observation information that represents that the position identified in Step S206 has been observed. In addition, the determination unit 186 sets information that represents that the position identified in Step S206 has been observed to the position (Step S212).

After Step S212, the display control unit 182 generates a graphic image signal of the observation information. Thereafter, the video signal processing circuit 12 combines the graphic image signal and a video signal and outputs the combined video signal to the display unit 5. The display unit 5 displays the observation information on the 3D model. In this way, the display unit 5 notifies a user that the position identified in Step S206 has been observed (Step S213).

When the determination unit 186 determines that the index value is not greater than the threshold value, the determination unit 186 generates observation information that represents that the position identified in Step S206 has not been observed (Step S214).

After Step S214, the display control unit 182 generates a graphic image signal of the observation information. Thereafter, processing similar to the processing in Step S213 is executed and the display unit 5 displays the observation information on the 3D model. In this way, the display unit 5 notifies a user that the position identified in Step S206 has not been observed (Step S215).

Figure 16:
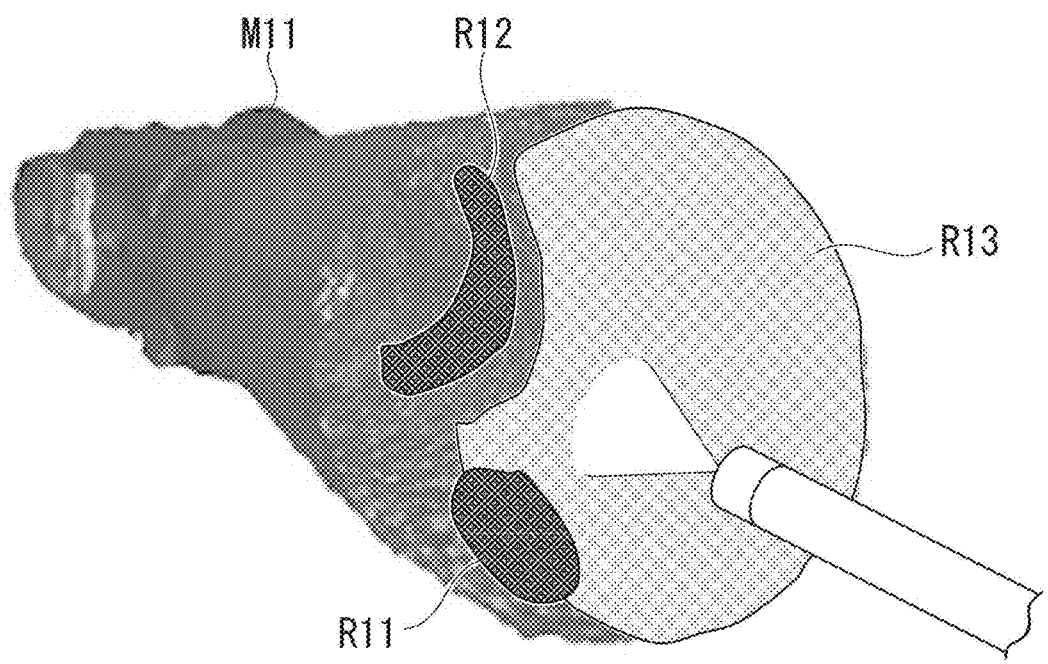
FIG. 16 is a diagram showing an example of an image displayed on the display unit according to the first embodiment of the present invention.

FIG. 16 shows an example of an image displayed on the display unit 5 in Step S215. As with the image shown in FIG. 13, a 3D model M11 is displayed on the display unit 5 and a region R11 of interest and a region R12 of interest are displayed on the 3D model M11. Further, a region R13 that has been observed is displayed on the 3D model M11. The region R13 corresponds to the observation information. For example, the region R13 is displayed in a color different from that of each of the region R11 of interest and the region R12 of interest. A region other than the region R13 in the 3D model M11 has not been observed. The region R13 may be translucently displayed such that a user can visually recognize the 3D model M11. As long as a user can distinguish between a region that has been observed and a region that has not been observed, any display method may be used.

Figure 17:
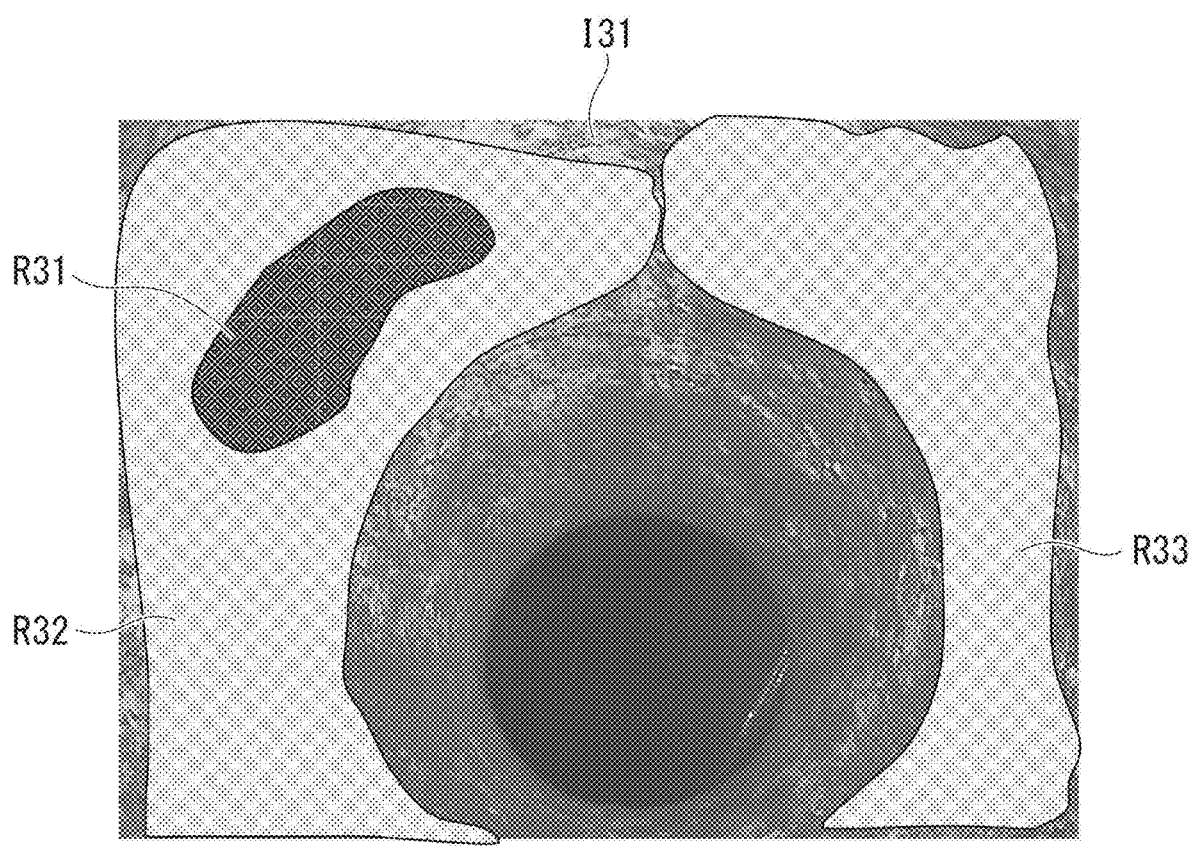
FIG. 17 is a diagram showing an example of an image displayed on the display unit according to the first embodiment of the present invention.

The observation information may be superimposed on the inspection image. FIG. 17 shows an example of an inspection image displayed on the display unit 5 in Step S215. An inspection image I31 is displayed on the display unit 5 and a region R31 of interest is displayed on the inspection image I31. Further, a region R32 and a region R33 that have been observed are displayed on the inspection image I31. The region R32 and the region R33 correspond to the observation information. A region other than the region R32 and the region R33 in the inspection image I31 has not been observed.

After Step S213 or Step S215, the main control unit 180 determines whether or not the processing of Steps S206 to S210 has been executed for all the pixels subjected to be processed (Step S216). When the main control unit 180 determines that the processing has not been executed for some of the pixels, Step S206 is executed.

When it is determined that the position on the 3D image has been observed in Step S207, Step S213 is executed without executing the processing for determining whether or not the position has been observed. After it is determined that the position on the 3D image has been observed, there is no case in which it is determined that the position has not been observed. When a new inspection image is processed, the setting that the position has been observed continues. Step S207 may be executed at any timing before Step S214 is executed.

In the above-described example, an index value is calculated for each pixel and observation information is generated for each pixel. An index value may be calculated for a plurality of pixels and observation information may be generated for the plurality of pixels. Pixels for which the above-described processing is executed may be thinned out. The above-described processing may be omitted for a pixel at the edge of the visual field.

When the main control unit 180 determines that the processing has been executed for all the pixels, the main control unit 180 determines whether or not the operation unit 4 has accepted completion of inspection from a user (Step S217). When the main control unit 180 determines that the operation unit 4 has not accepted the completion of inspection from a user, Step S203 is executed. When the main control unit 180 determines that the operation unit 4 has accepted the completion of inspection from a user, the inspection is completed.

The order of processing executed by the CPU 18a is not limited to the order shown in FIG. 11 and FIG. 12. For example, after the position and the posture of the camera are estimated in Step S205, the inspection image may be displayed in Step S204.

A method of operating an observation device according to each aspect of the present invention includes an image display step, an estimation step, an identification step, a determination step, and an observation information display step. The display control unit 182 displays an image of a subject inside the observation object on the display unit 5 in the image display step (Step S204). The camera position-posture estimation unit 184 estimates the position of the imaging device 28 and the posture of the imaging device 28 in the estimation step (Step S205). The position and the posture are a position and a posture, respectively, when the imaging device 28 acquires the image. In the identification step (Step S206), the position identification unit 185 identifies the position on the 3D model corresponding to a pixel of the image on the basis of the position and the posture that are estimated in the estimation step. The determination unit 186 determines whether or not the imaging condition that has been set in the region of interest (first region) or the general region (second region) including the position on the 3D model is satisfied in the determination step (Step S211). In the observation information display step (Step S213 and Step S215), the display control unit 182 displays observation information on the display unit 5 on the basis of a result of determination executed by the determination unit 186. The observation information represents whether or not the region of interest or the general region including the position on the 3D model has been observed.

When the determination unit 186 determines that the imaging condition is satisfied, the display control unit 182 displays observation information that represents that the imaging condition is satisfied on the display unit 5 in the observation information display step (Step S213). On the other hand, when the determination unit 186 determines that the imaging condition is not satisfied, the display control unit 182 may display observation information that represents that the region of interest or the general region including the position on the 3D model has not been observed on the display unit 5 in the observation information display step (Step S215).

In the first embodiment, when the imaging condition suitable for the region of interest is satisfied, it is determined that the region of interest has been observed. The endoscope device 1 can determine whether or not a region of a subject has been observed on the basis of the condition of each region. Since a result of the determination is visualized, the endoscope device 1 can offer an observation assistance function having the high reliability to a user.

(First Modified Example of First Embodiment)

A first modified example of the first embodiment of the present invention will be described. The PC 41 executes the processing shown in FIG. 5 in the first embodiment. The CPU 18*a* of the endoscope device 1 includes at least part of the functions of the CPU 43 of the PC 41 in the first modified example of the first embodiment. The CPU 18*a* of the endoscope device 1 executes at least part of the processing shown in FIG. 5 and FIG. 10.

For example, the CPU 18*a* of the endoscope device 1 may include a condition setting unit (imaging condition setting unit) similar to the condition setting unit 437 of the CPU 43. The condition setting unit of the CPU 18*a* sets an imaging condition to each of a region of interest and a general region in an imaging condition setting step (Step S107).

The CPU 18*a* of the endoscope device 1 may include a region acceptance unit similar to the region acceptance unit 434 of the CPU 43. The region acceptance unit of the CPU 18*a* sets a region of interest and a general region to a 3D model in a region setting step (Step S105). The region setting step is executed before the imaging condition setting step is executed.

The CPU 18*a* of the endoscope device 1 may include a 3D model generation unit (processing unit) similar to the 3D model generation unit 432 of the CPU 43. The 3D model generation unit of the CPU 18*a* detects a feature point in each of a plurality of images acquired by the imaging device 28 in a feature point detection step (Step S103*a*). The 3D model generation unit of the CPU 18*a* associates the feature point in each of the plurality of images between the images in an association step (Step S103*b*). The 3D model generation unit of the CPU 18*a* calculates the position of the imaging device 28 and the posture of the imaging device 28 on the basis of the feature point in a calculation step (Step S103*c*). The 3D model generation unit of the CPU 18*a* generates a 3D model on the basis of the position of the imaging device 28 and the posture of the imaging device 28 in a generation step (Step S103*d*). Before the region setting step is executed, the feature point detection step, the association step, the calculation step, and the generation step are executed.

(Second Modified Example of First Embodiment)

A second modified example of the first embodiment of the present invention will be described. In the first embodiment, the case in which a user designates a region of interest is described. The present invention is not limited to the case in which a region of interest designated by a user is set. The PC 41 or the endoscope device 1 may automatically detect a region of interest in an image and may set the detected region of interest to a 3D model.

In the first embodiment, the case in which a user designates an imaging condition is described. The present invention is not limited to the case in which an imaging condition designated by a user is set. The PC 41 or the endoscope device 1 may automatically generate an imaging condition and may set the generated imaging condition to a 3D model.

Figure 18:
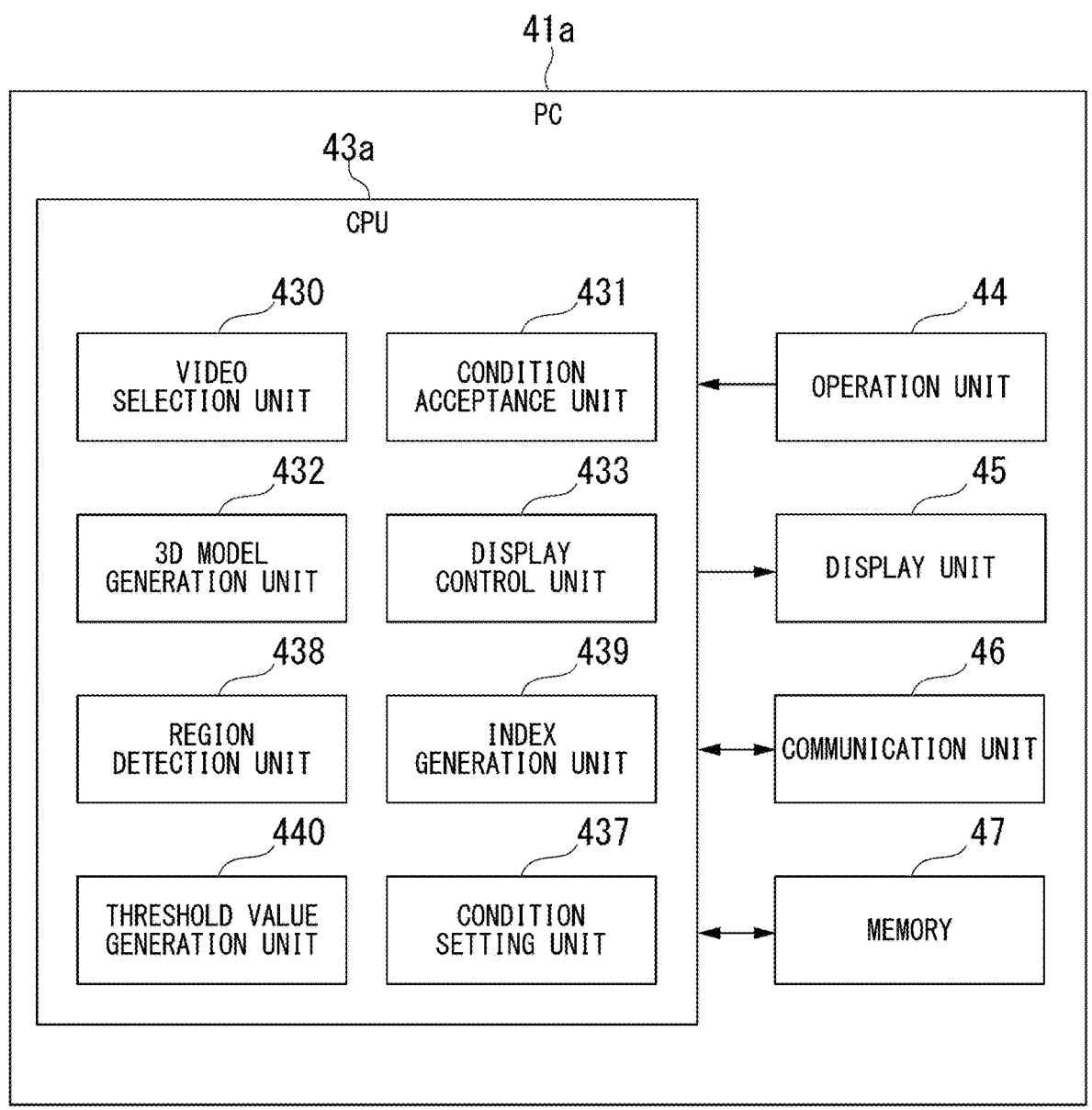
FIG. 18 is a block diagram showing a functional configuration of a PC according to a second modified example of the first embodiment of the present invention.

The PC 41 shown in FIG. 3 is changed to a PC 41*a* shown in FIG. 18. FIG. 18 shows a functional configuration of the PC 41*a*. The same configuration as the configuration shown in FIG. 3 will not be described.

The CPU 43 shown in FIG. 3 is changed to a CPU 43*a*. The functions of the CPU 43*a* are constituted by a video selection unit 430, a condition acceptance unit 431, a 3D model generation unit 432, a display control unit 433, a region detection unit 438, an index generation unit 439, a threshold value generation unit 440, and a condition setting unit 437. At least one of the blocks in the CPU 43*a* shown in FIG. 18 may be constituted by a circuit different from the CPU 43*a*.

Each unit in the CPU 43*a* may be constituted by at least one of a processor and a logic circuit. Each unit in the CPU 43*a* may include one or a plurality of processors. Each unit in the CPU 43*a* may include one or a plurality of logic circuits.

The region detection unit 438 automatically detects a region of interest and a general region on the basis of an image acquired by the imaging device 28. For example, the region detection unit 438 detects a region of interest by using a technical means such as machine learning. The region detection unit 438 classifies the detected region as a region of interest and classifies a region other than the region of interest as a general region. The region detection unit 438 sets the region of interest and the general region to a 3D model generated by the 3D model generation unit 432. Each region set by the region detection unit 438 is stored on the memory 47.

In processing in which the region detection unit 438 detects a region of interest and a general region, input of information that represents a region of interest and a general region from a user is not accepted. Therefore, even if a user operates the operation unit 4, the user is unable to input information that designates each region to the operation unit 4. The operation unit 4 stops acceptance of the information.

The index generation unit 439 automatically generates an index on the basis of an image acquired by the imaging device 28. Specifically, the index generation unit 439 identifies a type of a subject seen in a region of interest in an inspection image. For example, the type of the subject is a cooling hole, an edge, a welding trace of a pipe, or the like. The index generation unit 439 generates an index suitable for the identified type of the subject. The threshold value generation unit 440 automatically generates a threshold value of the index generated by the index generation unit 439.

In processing in which the index generation unit 439 generates an index and in processing in which the threshold value generation unit 440 generates a threshold value, input of an imaging condition from a user is not accepted. Therefore, even if a user operates the operation unit 4, the user is unable to input information that designates an index and a threshold value to the operation unit 4. The operation unit 4 stops acceptance of the imaging condition.

Figure 19:
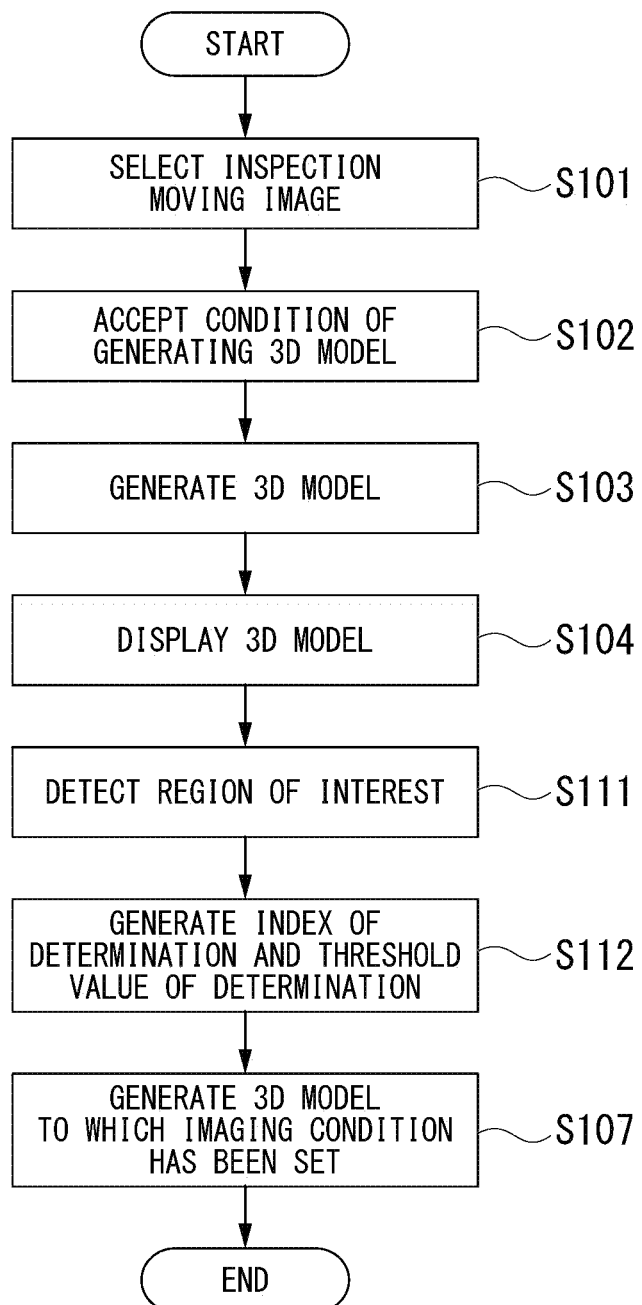
FIG. 19 is a flow chart showing a procedure of processing executed by the PC according to the second modified example of the first embodiment of the present invention.

FIG. 19 shows a procedure of processing executed by the PC 41*a*. The same processing as the processing shown in FIG. 5 will not be described. Hereinafter, an example in which an inspection image included in an inspection moving image selected in Step S101 is used will be described. When the processing described below is executed, any one of a moving image and a still image may be used.

After Step S104, the region detection unit 438 detects a region of interest. The region detection unit 438 classifies a region other than the region of interest as a general region. The region detection unit 438 sets the region of interest and the general region to the generated 3D model (Step S111).

For example, the region detection unit 438 detects a first region from an inspection image. The detected first region is similar to a region of all or part of an image used for measurement by a user in the past. Alternatively, the region detection unit 438 detects a second region from the inspection image. Annotation (meta data) embedded in an image or a specific position in an image as an inspection record by a user is present in the detected second region. Alternatively, the region detection unit 438 detects a third region from another inspection image prepared for region setting. The detected third region is similar to a region designated on the inspection image by a user.

A specific example of a procedure for setting a region of interest by using the machine learning will be described. A region that should be detected as a region of interest is defined. The region is a region for which measurement has actually been performed in a measurement image or a region to which annotation has been given. A user manages the measurement image on the basis of the past inspection. The measurement image is input to the PC 41a as teacher data with a correct answer that should be detected as a region of interest of the machine learning. The region detection unit 438 learns a region of interest by using the teacher data. When a certain inspection image is input to the PC 41a, the region detection unit 438 performs detection of a region of interest. If there is a region of interest in a subject seen in the inspection image, it is possible for the region detection unit 438 to output the region of interest.

The region detection unit 438 may execute more complicated processing than simple processing for determining whether or not there is a region of interest. For example, the region detection unit 438 may classify the type of a detected region of interest. It is possible for the region detection unit 438 to classify a detected region of interest as a flaw present at an edge portion of a blade, a flaw present in a cooling hole, or the like. By using this method, it is possible for the region detection unit 438 to automatically set a region of interest regardless of an instruction from a user.

After Step S111, the index generation unit 439 automatically generates an index of each of the region of interest and the general region. The threshold value generation unit 440 generates a threshold value of the index of each region (Step S112). After Step S112, Step S107 is executed.

For example, the index generation unit 439 classifies the type of a subject seen in the region of interest by performing image processing. The index generation unit 439 may use the type of the subject classified by the region detection unit 438. An index and a threshold value are stored on the memory 47 for each type of a subject in advance. The index generation unit 439 reads an index corresponding to the type of the subject from the memory 47. This index is to be set to the region of interest. The threshold value generation unit 440 reads a threshold value corresponding to the type of the subject from the memory 47. This threshold value is to be set to the region of interest.

As with an index and a threshold value of the region of interest, an index and a threshold value of the general region are stored on the memory 47 in advance. The index generation unit 439 reads an index of the general region from the memory 47 and the threshold value generation unit 440 reads a threshold value of the general region from the memory 47.

The CPU 18a of the endoscope device 1 may include at least part of the functions of the CPU 43a of the PC 41a. The CPU 18a of the endoscope device 1 may execute at least part of the processing shown in FIG. 19.

For example, the CPU 18a of the endoscope device 1 may include a region detection unit similar to the region detection unit 438 of the CPU 43a. The CPU 18a of the endoscope device 1 may include an index generation unit similar to the index generation unit 439 of the CPU 43a. The CPU 18a of the endoscope device 1 may include a threshold value generation unit similar to the threshold value generation unit 440 of the CPU 43a.

In the second modified example of the first embodiment, a region of interest and an imaging condition are automatically set. For this reason, the burden of a user is eased.

Second Embodiment

A second embodiment of the present invention will be described. The endoscope device 1 according to the second embodiment has three functions described below in addition to the function in the first embodiment. The three functions are useful when a user inspects an inspection object. The endoscope device 1 does not need to have all of the three functions. A case in which the endoscope device 1 has only one or two of the three functions described below is included in the scope of the present invention.

When it is determined that a region of interest or a general region has not been observed, the endoscope device 1 notifies a user of a cause of the determination that the region has not been observed (first function). The first function may include a function of notifying a user of a method of changing an imaging condition such that it is determined that a region of interest or a general region has been observed in consideration of the cause of the determination that the region has not been observed. When it is determined that a position on a 3D model has not been observed and the position is behind a visual field of the imaging device 28, the endoscope device 1 notifies a user that there is a region of interest or a general region that has not been observed (second function). The endoscope device 1 automatically records an inspection image in which a region of interest that has been observed is seen (third function).

Figure 20:
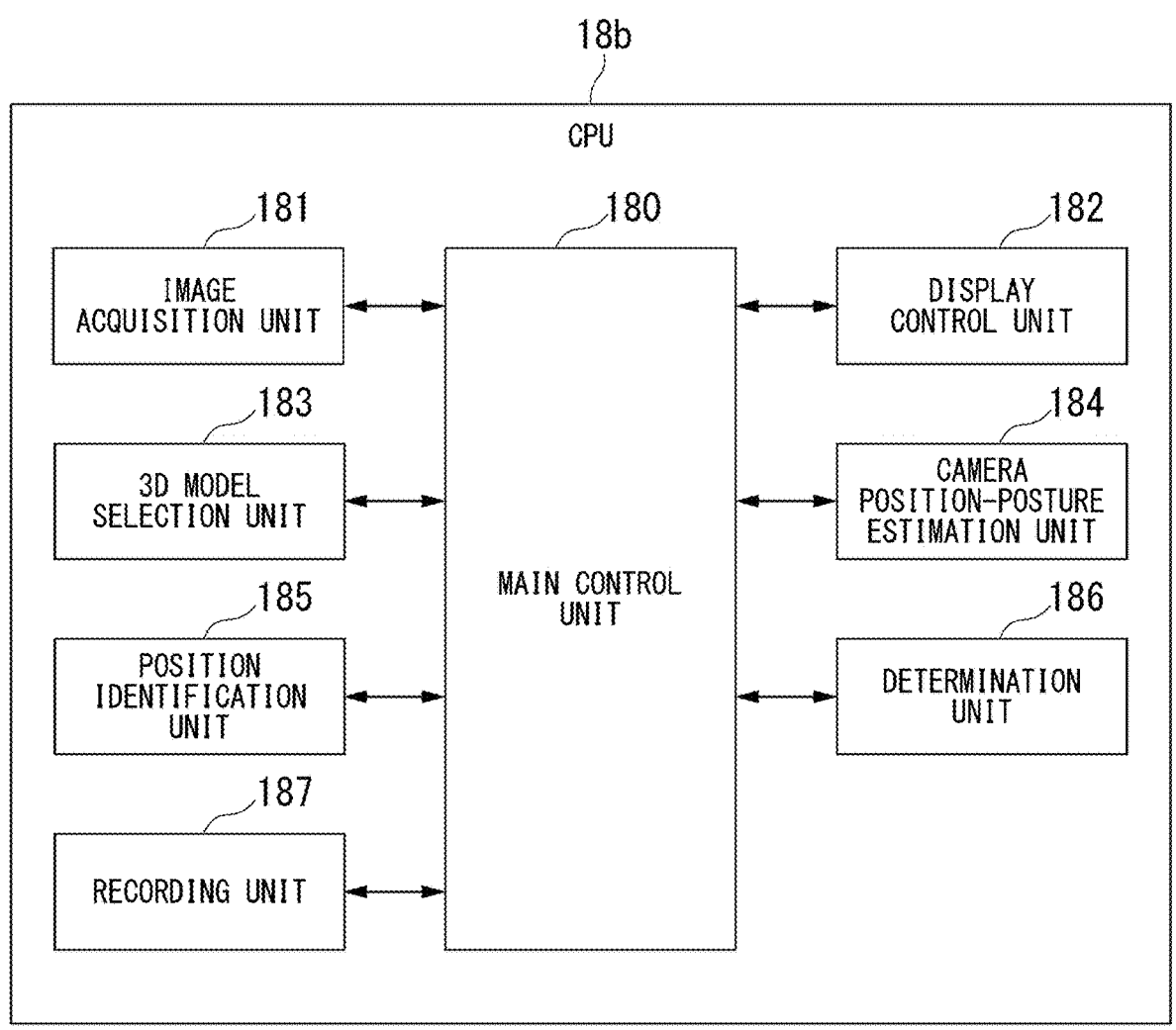
FIG. 20 is a block diagram showing a functional configuration of a CPU according to a second embodiment of the present invention.

The CPU 18a shown in FIG. 4 is changed to a CPU 18b shown in FIG. 20. FIG. 20 shows a functional configuration of the CPU 18b. The same configuration as the configuration shown in FIG. 4 will not be described.

The functions of the CPU 18b are constituted by a main control unit 180, an image acquisition unit 181, a display control unit 182, a 3D model selection unit 183, a camera position-posture estimation unit 184, a position identification unit 185, a determination unit 186, and a recording unit 187. At least one of the blocks shown in FIG. 20 may be constituted by a circuit other than the CPU 18b.

Each unit shown in FIG. 20 may be constituted by at least one of a processor and a logic circuit. Each unit shown in FIG. 20 may include one or a plurality of processors. Each unit shown in FIG. 20 may include one or a plurality of logic circuits.

An imaging condition includes a plurality of conditions. Therefore, an imaging condition includes a plurality of indices and a threshold value of each index. When the determination unit 186 determines that at least one condition included in the plurality of conditions is not satisfied, the display control unit 182 displays condition information that represents the at least one condition on the display unit 5. In this way, the display unit 5 notifies a user of the at least one condition that is a cause of the determination that a position on a 3D model has not been observed.

The display control unit 182 may display information that represents a specific method of changing an imaging condition such that it is determined that the position on the 3D model has been observed on the display unit 5. For example, when the object distance is large and it is determined that the position on the 3D model has not been observed, the display control unit 182 may display a message "The present object distance is OO mm. Please perform observation such that the object distance becomes XX mm." on the display unit 5. When the type of an optical adaptor is the cause of the determination that the position on the 3D model has not been observed, the display control unit 182 may display a message "Please change the type of the optical adaptor from direct view to side view." on the display unit 5.

RAM 14 stores a non-observed position that is a position on a 3D model for which it is determined that an imaging condition is not satisfied. When the non-observed position is behind a visual field of the imaging device 28, the display control unit 182 displays first notification information that represents that there is a region of interest or a general region including the non-observed position on the display unit 5. The position behind the visual field of the imaging device 28 is not in the visual field. The position behind the visual field of the imaging device 28 is a position on a 3D model away from a position within the visual field toward a viewpoint.

For example, a position on a 3D model corresponding to a first inspection image is identified and it is determined that the position has not been observed. The position is stored on the RAM 14. After the first inspection image is acquired, a second inspection image is acquired. When there is a non-observed position behind a visual field of the imaging device 28 at the time of acquiring the second inspection image, the display control unit 182 displays the first notification information on the display unit 5.

When the determination unit 186 determines that an imaging condition that has been set to a region of interest is satisfied, the recording unit 187 records an inspection image in which a region corresponding to the region of interest on a 3D model is seen. For example, the recording unit 187 records the inspection image on the memory card 42. Therefore, the inspection image in which the region of interest that has been observed is seen is recorded.

Figure 21:
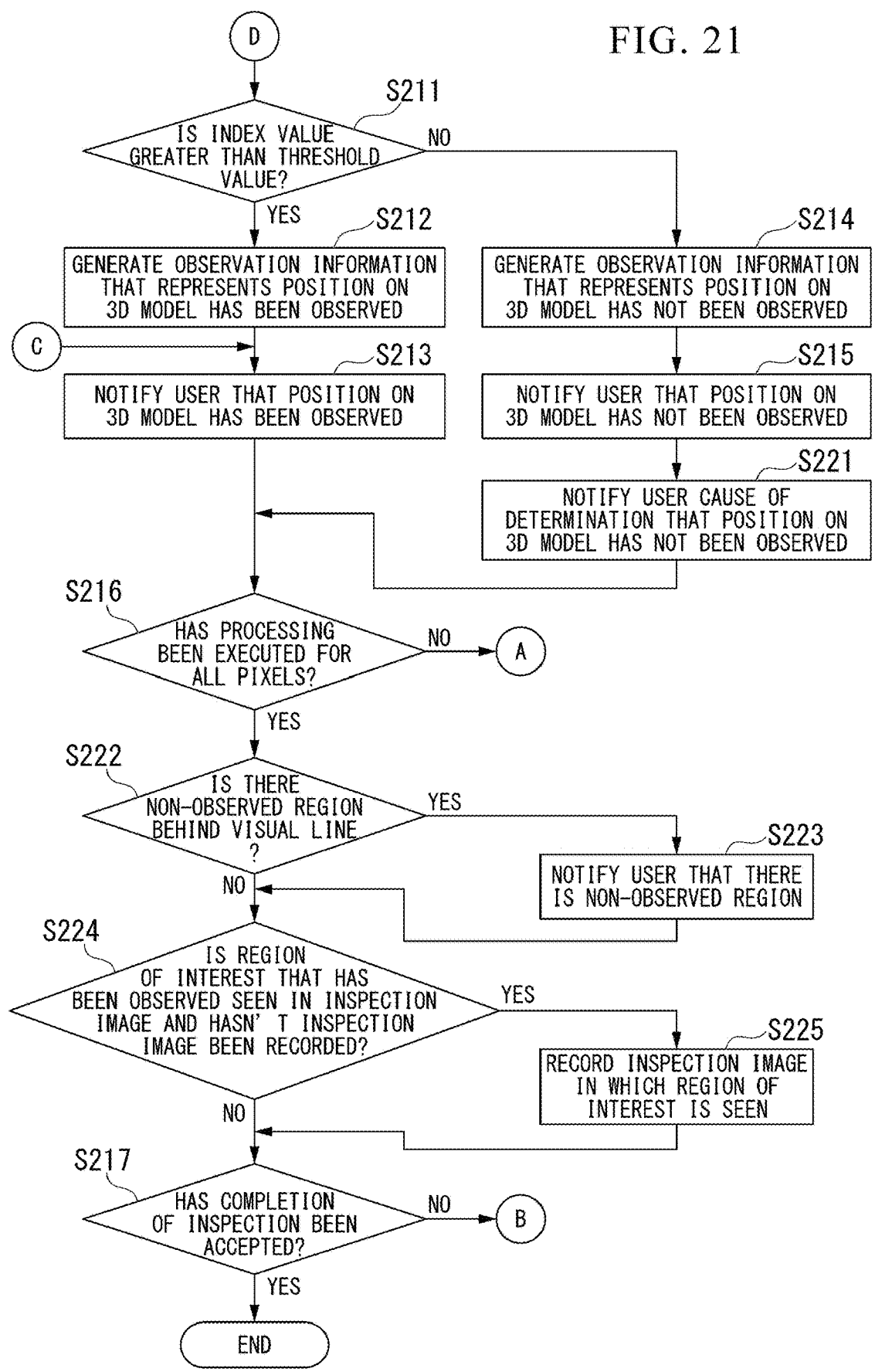
FIG. 21 is a flow chart showing a procedure of processing executed by the CPU according to the second embodiment of the present invention.

The processing shown in FIG. 12 is changed to processing shown in FIG. 21. A procedure of processing executed during inspection will be described with reference to FIG. 21. FIG. 21 shows a procedure of processing executed by the CPU 18b. The same processing as the processing shown in FIG. 12 will not be described.

In a case in which the determination unit 186 determines that an index value is not greater than a threshold value in Step S211, a non-observed position exists. In such a case, it is notified to a user that a position on a 3D model has not been observed in Step S215.

After Step S215, the determination unit 186 notifies the display control unit 182 of an index of which a value does not exceed a threshold value in Step S211. The display control unit 182 generates a graphic image signal for displaying the non-observed position in a color corresponding to the index. Thereafter, the video signal processing circuit 12 combines the graphic image signal and a video signal and outputs the combined video signal to the display unit 5. The display unit 5 displays the non-observed position on the 3D model in a predetermined color. The non-observed position is displayed in a color corresponding to a predetermined index. The color corresponds to the condition information.

In this way, the display unit 5 notifies a user of a cause of the determination that the position on the 3D model has not been observed (Step S221). After Step S221, Step S216 is executed.

Figure 22:
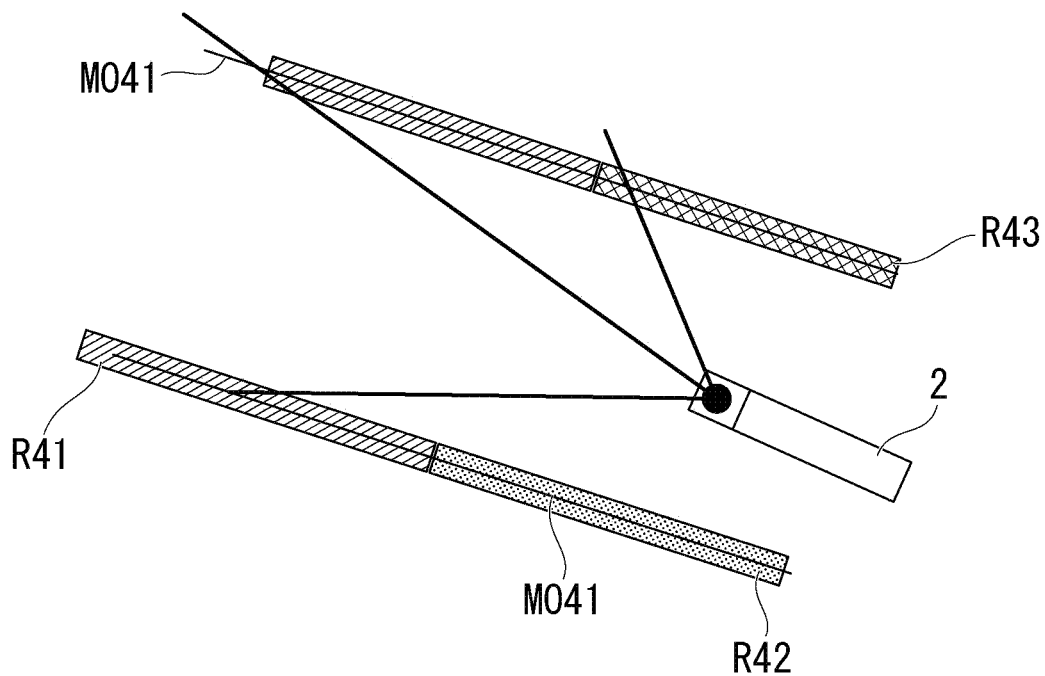
FIG. 22 is a diagram showing a method of notifying a user of a cause of determination that a position on a three-dimensional model has not been observed in the second embodiment of the present invention.

Details of Step S221 will be described with reference to FIG. 22. FIG. 22 shows a method of notifying a user of a cause of the determination that the position on the 3D model has not been observed. A 3D model MO41 has a tube shape. A cross section passing through the center axis of the 3D model MO41 is shown in FIG. 22. A state in which the insertion unit 2 is virtually inserted into the 3D model MO41 is shown in FIG. 22.

A region R41 is a region for which it is determined by the determination unit 186 that the region has been observed. A region R42 is a region for which a value of the index A in FIG. 6 does not exceed a threshold value and it is determined by the determination unit 186 that the region has not been observed. A region R43 is a region for which a value of the index B in FIG. 6 does not exceed a threshold value and it is determined by the determination unit 186 that the region has not been observed.

In the first embodiment, the display unit 5 displays observation information that represents that the region R42 and the region R43 have not been observed. In the first embodiment, the region R42 and the region R43 are displayed in a color different from that of the region R41. For this reason, a user can know that the region R42 and the region R43 have not been observed. In the first embodiment, the color of the region R42 and the color of the region R43 are the same. For this reason, a user is unable to know why it is determined that the region R42 and the region R43 have not been observed. A user is unable to determine under what kind of conditions an observation object should be observed when the observation object is observed again. Therefore, a user is unable to know how the imaging condition is to be changed.

In the second embodiment, the region R42 is displayed in a color assigned to the index A and the region R43 is displayed in a color assigned to the index B. The color assigned to each of the index A and the index B is different from the color for displaying a region for which it is determined that the region has been observed. A user can know a cause of the determination that a region has not been observed. When the region is observed again, a user can observe a subject paying attention to the cause. In addition, a user can know how the imaging condition is to be changed.

A character or the like that represents an index of which a value does not exceed a threshold value may be displayed on the display unit 5. As long as a user can understand a cause of the determination that a region has not been observed, any notification method may be used.

When the main control unit 180 determines that the processing has been executed for all the pixels in Step S216, the determination unit 186 determines whether or not the non-observed position is behind a visual field of the imaging device 28 (Step S222). When the non-observed position is not behind the visual field of the imaging device 28, Step S224 is executed.

When the non-observed position is behind the visual field of the imaging device 28, the display control unit 182 generates a graphic image signal for displaying first notification information that represents that there is a region including a non-observed position. Thereafter, the video signal processing circuit 12 combines the graphic image signal and a video signal and outputs the combined video signal to the display unit 5. The display unit 5 displays the first notification information on the 3D model. The first notification information is a character or the like. In this way, the display unit 5 notifies a user that there is a region including a non-observed position behind the visual field of the imaging device 28 (Step S223).

The fact that there is a region including a non-observed position may be notified to a user by voice. As long as a user can understand that there is a region including a non-observed position, any display method may be used.

In Step S211, it is determined whether or not a position on the 3D model has been observed. When it is determined that the position on the 3D model has not been observed, information that represents that the position has not been observed is set to the position in Step S214. The determination unit 186 determines whether or not the position to which the information has been set exists on the 3D model in Step S222. When the position exists, the determination unit 186 determines that the position is a non-observed position. Further, the determination unit 186 determines whether or not the non-observed position is behind a visual field of the imaging device 28 in Step S222.

Figure 23:
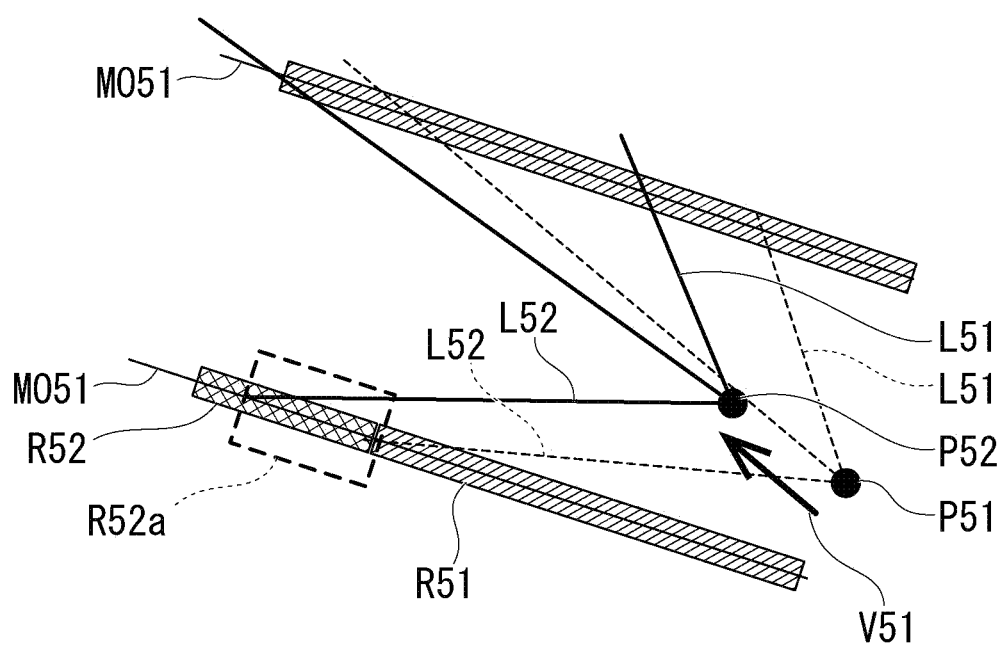
FIG. 23 is a diagram showing a method of detecting a non-observed position behind a visual field of an imaging device in the second embodiment of the present invention.

Details of Step S222 will be described with reference to FIG. 23. FIG. 23 shows a method of detecting a non-observed position behind a visual field of the imaging device 28. A 3D model MO51 has a tube shape. A cross section passing through the center axis of the 3D model MO51 is shown in FIG. 23. A region R51 is a region for which it is determined by the determination unit 186 that the region has been observed. A position P51 is a position of a camera estimated on the basis of a first inspection image. A position P52 is a position of the camera estimated on the basis of a second inspection image acquired following the first inspection image. The position P52 is the current position of the camera. A motion vector V51 represents the motion between the position P51 and the position P52.

When the position P51 and the position P52 are estimated, it is possible to calculate the motion vector V51. The motion vector V51 represents a traveling direction of the camera. A line L51 and a line L52 represent visual lines passing through both ends of the visual field of the imaging device 28. When the first inspection image acquired at the time at which the camera is at the position P51 is processed, it is determined that a region R52 has not been observed. When the second inspection image acquired at the time at which the camera is at the position P52 is processed, it is also determined that a region R52 has not been observed. When the camera is at the position P52, a region R52a is out of the visual field of the imaging device 28. The region R52a is part of the region R52. The region R52a has not been observed and is behind the visual field of the imaging device 28.

In a case in which the camera continues to travel in the direction of the motion vector V51, there is a possibility that a user misses an opportunity of observing the inspection object. For this reason, it is notified to a user that there is a region including a non-observed position in Step S223.

After Step S223, the determination unit 186 determines whether or not a region of interest that has been observed is seen in an inspection image. In addition, the determination unit 186 determines whether or not the inspection image including the region of interest has been recorded (Step S224). When the determination unit 186 determines that the region of interest that has been observed is not seen in the inspection image, Step S217 is executed. Alternatively, when the determination unit 186 determines that the inspection image including the region of interest that has been observed has been recorded, Step S217 is executed.

When the determination unit 186 determines that the region of interest that has been observed is seen in the inspection image and the determination unit 186 determines that the inspection image including the region of interest has not been recorded, the recording unit 187 records the inspection image (Step S225). In this way, the evidence that a user has observed the region of interest remains. After Step S225, Step S217 is executed.

Any one of a moving image and a still image may be recorded. In a case in which a moving image is recorded, a moving image from a timing at which a region of interest moves in to a timing at which the region of interest moves out may be recorded. In a case in which a still image is recorded, a still image in which a region of interest is the largest in a visual field may be recorded. Alternatively, a still image having the largest covering rate may be recorded. The covering rate is defined as a ratio of a second area to a first area. The first area is the entire area of the defined region of interest. The second area is the area of a region of interest seen in an inspection image. There is no need to record only one still image. A plurality of still images may be recorded.

The display control unit 182 may display a non-observed position on an inspection image in Step S221. The display control unit 182 may display first notification information that represents that there is a region including a non-observed position on an inspection image in Step S223.

When the determination unit 186 determines that an imaging condition set in a general region is satisfied, the recording unit 187 may record an inspection image in which a region corresponding to a general region on a 3D model is seen.

A method of operating an observation device according to each aspect of the present invention may include a condition information display step. An imaging condition includes a plurality of conditions. When the determination unit 186 determines that at least one condition is not satisfied, the display control unit 182 displays condition information that represents the at least one condition on the display unit 5 in the condition information display step (Step S221).

A method of operating an observation device according to each aspect of the present invention may include a first notification information display step. When a non-observed position is behind a visual field of the imaging device 28, the display control unit 182 displays first notification information that represents that there is a region including the non-observed position on the display unit 5 in the first notification information display step (Step S223).

A method of operating an observation device according to each aspect of the present invention may include a recording step. When the determination unit 186 determines that an imaging condition set in a region of interest is satisfied, the recording unit 187 records an inspection image in which a region corresponding to the region of interest is seen in the recording step (Step S225).

In the second embodiment, the endoscope device 1 offers following three functions. The endoscope device 1 notifies a user of a cause of the determination that a region has not been observed. The endoscope device 1 notifies a user that a region that has not been observed is behind a visual field of the imaging device 28. The endoscope device 1 records an inspection image in which a region of interest that has been observed is seen. Since these functions are added, an inspection time can be expected to be shortened. In addition, the endoscope device 1 can offer an observation assistance function having the higher reliability to a user.

Third Embodiment

A third embodiment of the present invention will be described. In the first embodiment, two states are discriminated. A first state is a state in which a region has been observed. A second state is a state in which a region has not been observed. In the third embodiment, reliability according to the degree to which a region has been observed is calculated. The reliability can be configured to represent any one of two or more states.

The endoscope device 1 according to the third embodiment includes the CPU 18a shown in FIG. 4. The determination unit 186 calculates reliability (evaluation value) that represents the degree to which an imaging condition set in a region of interest or a general region is satisfied. The display control unit 182 displays the reliability as observation information on the display unit 5. The observation information represents whether or not a region of interest or a general region including a position on a 3D model has been observed.

The determination unit 186 determines whether or not an imaging condition is satisfied by comparing the reliability with a threshold value. This threshold value is not necessarily the same as a threshold value used for determination of an index value. When the determination unit 186 determines that the imaging condition is not satisfied, the display control unit 182 displays second notification information that represents a region of interest or a general region including a position on a 3D model has not been observed on the display unit 5.

Figure 24:
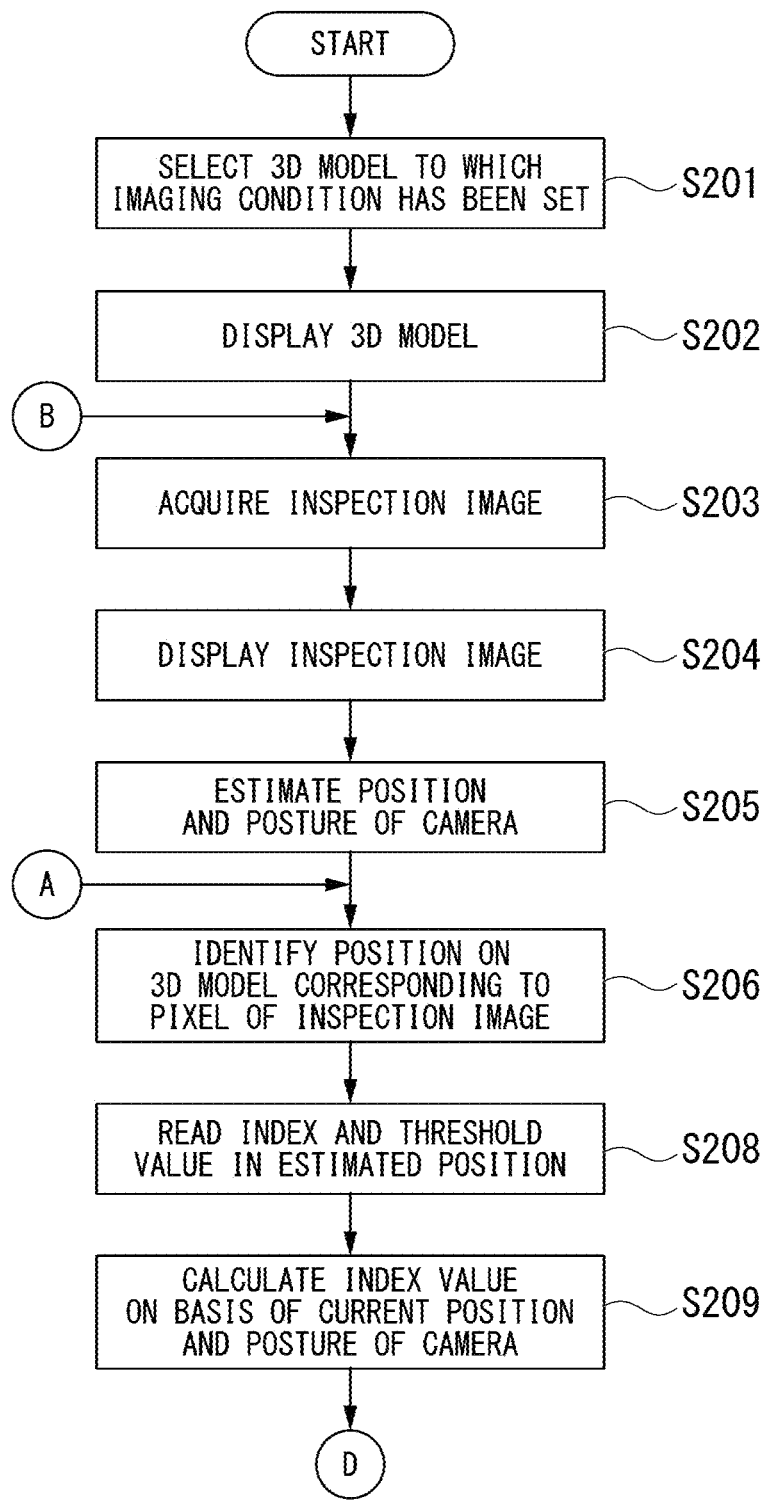
FIG. 24 is a flow chart showing a procedure of processing executed by a CPU according to a third embodiment of the present invention.
Figure 25:
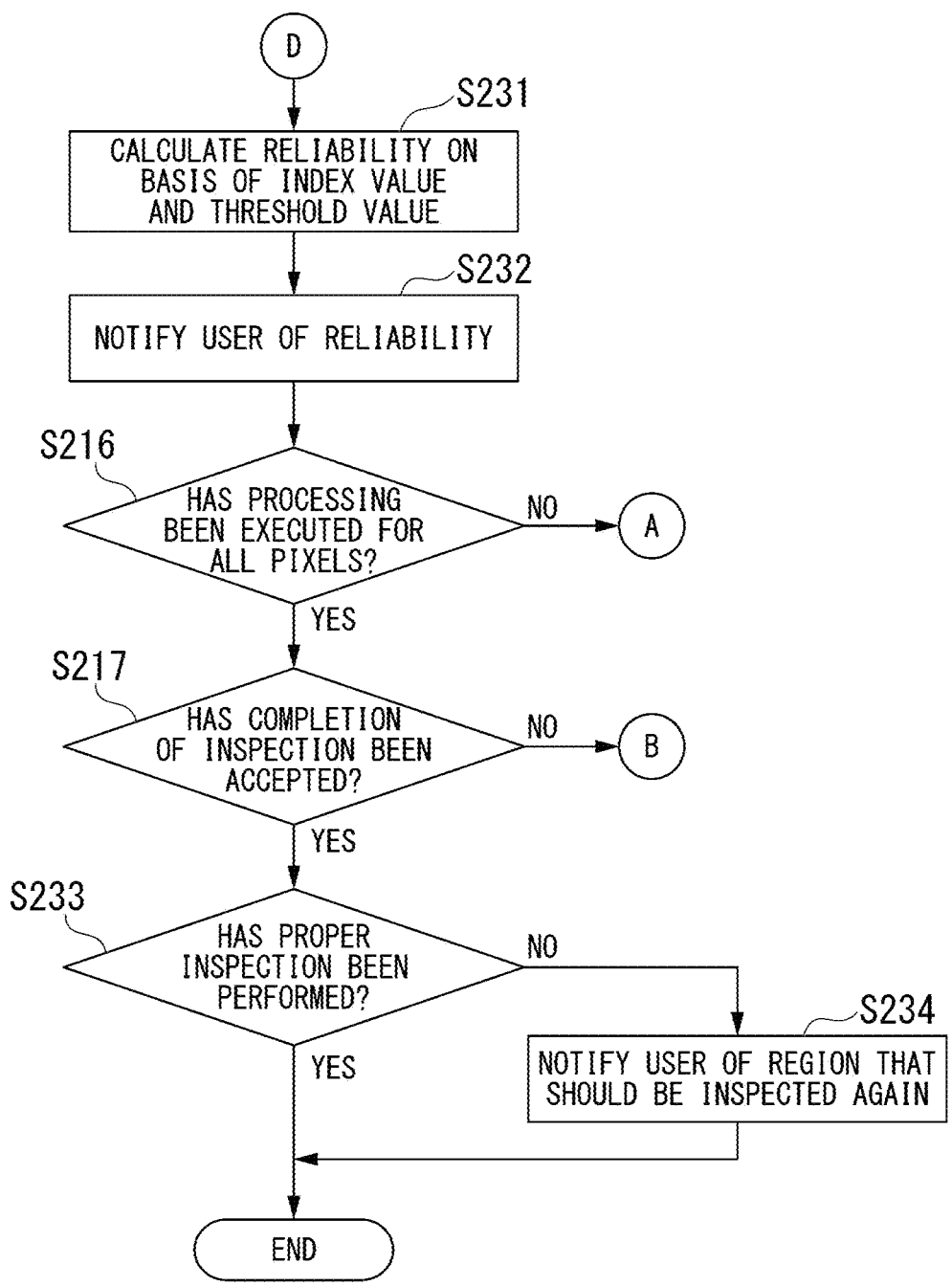
FIG. 25 is a flow chart showing a procedure of processing executed by the CPU according to the third embodiment of the present invention.

The processing shown in FIG. 11 is changed to processing shown in FIG. 24. The processing shown in FIG. 12 is changed to processing shown in FIG. 25. A procedure of processing executed during inspection will be described with reference to FIG. 24 and FIG. 25. FIG. 24 and FIG. 25 show a procedure of processing executed by the CPU 18a. The same processing as the processing shown in FIG. 11 and FIG. 12 will not be described.

After Step S206, Step S208 is executed. Step S207 shown in FIG. 11 is not executed.

After Step S209, the determination unit 186 calculates reliability on the basis of the index value calculated in Step S209 and the threshold value read in Step S208 (Step S231). The reliability is defined such that the reliability of a position on a 3D model becomes higher as the possibility that a user has observed a region including the position becomes higher. In a case in which the reliability of a position on a 3D model is high, the possibility that a user has observed a region including the position is high. In a case in which the reliability of a position on a 3D model is low, the possibility that a user has observed a region including the position is low. For example, the reliability has a value ranging from 0% to 100%. In a case in which the reliability is 100%, a region of interest or a general region has been observed.

For example, the determination unit 186 calculates reliability by using following Expression (4).

$$E_t = \sum_{i=0}^{N} w_i \frac{e_i}{Th_i} \quad (4)$$

In Expression (4), reliability in a certain time point t is expressed as $E_t$ and a weight attached to an i-th index is expressed as $W_i$. In Expression (4), a value of the i-th index is expressed as $e_i$ and a threshold value of the i-th index is expressed as $Th_i$. The determination unit 186 calculates reliability of each position on a 3D model in the time point t. The determination unit 186 repetitively calculates the reliability of each position until inspection is completed.

In a case in which the maximum value of the reliability $E_t$ is updated from the start of inspection to the end of the inspection, the value is stored on the RAM 14. An example in which a point of an inspection object is paid attention to. It is assumed that the tip end 20 of the insertion unit 2 moves from a first position to a second position and further moves to a third position. The first position and the third position are far from a point of an inspection object. The second position is close to the point of the inspection object. In a case in which the tip end 20 of the insertion unit 2 moves like this, the maximum value of the reliability is held. Updating a value of the reliability to a low value is avoided. The determination unit 186 may calculate the sum of reliability at each time point for each position on a 3D model. The sum may be defined as the final reliability.

After Step S231, the display control unit 182 generates a graphic image signal for displaying reliability. Thereafter, the video signal processing circuit 12 combines the graphic image signal and a video signal and outputs the combined video signal to the display unit 5. The display unit 5 displays observation information on an inspection image. Each of a region of interest and a general region is displayed in a color corresponding to the reliability of each region. The color corresponds to the observation information. In this way, the display unit 5 notifies a user of the reliability of the position identified in Step S206 (Step S232). After Step S232, Step S216 is executed.

Figure 26:
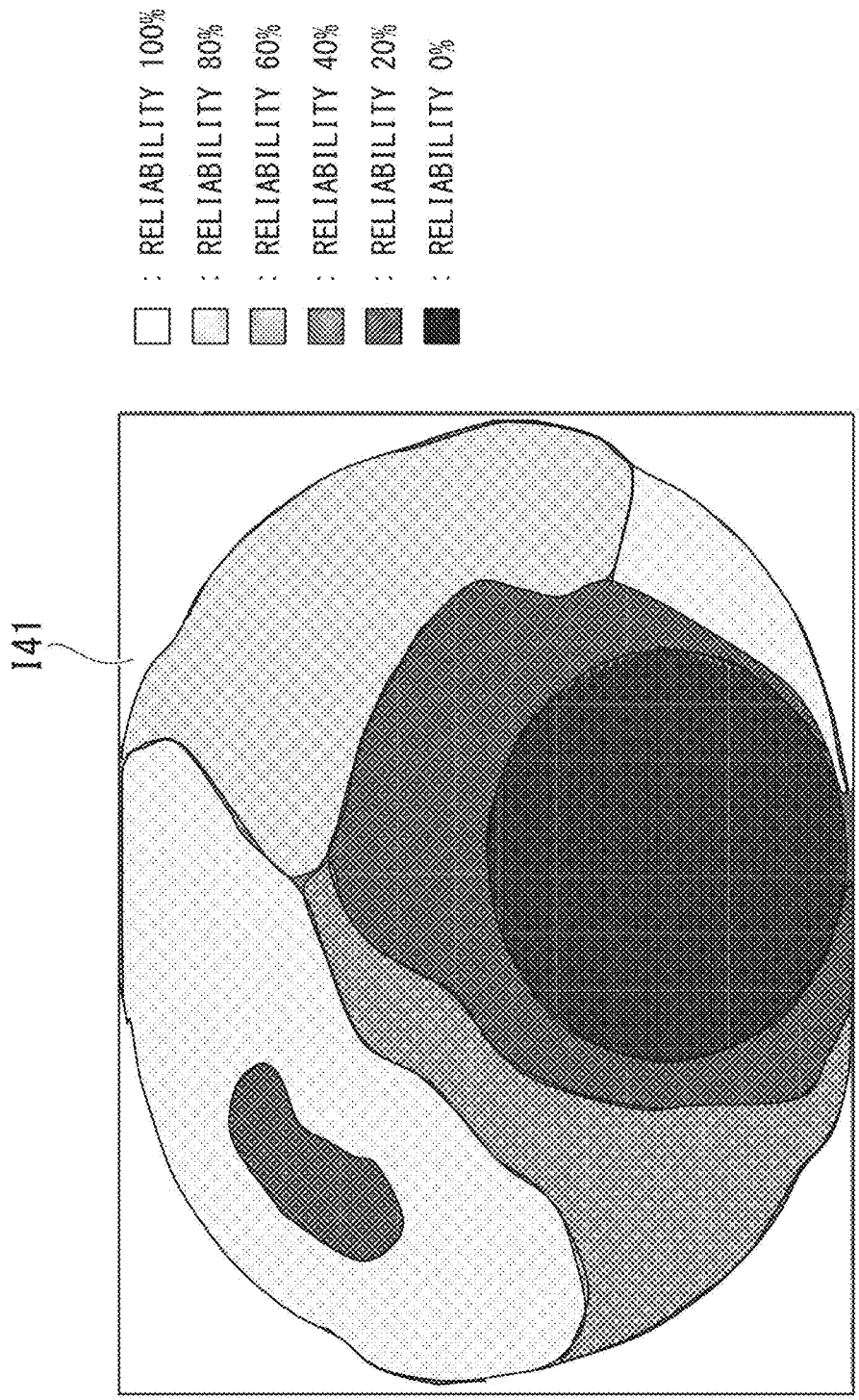
FIG. 26 is a diagram showing an example of an image displayed on a display unit according to the third embodiment of the present invention.

FIG. 26 shows an example of an inspection image displayed on the display unit 5 in Step S232. An inspection image I41 is displayed on the display unit 5. Further, each of a region of interest and a general region is displayed in a color corresponding to the reliability of each region. While reliability is displayed on an inspection image, there is a possibility that a pattern of a subject is hard to be seen. For this reason, the endoscope device 1 may have a function of switching between on and off of display of reliability on the basis of an instruction from a user. There is no need for second notification information to be superimposed on an inspection image. As long as a user can understand reliability, any display method may be used.

When the main control unit 180 determines that the operation unit 4 has accepted completion of inspection from a user in Step S217, the determination unit 186 determines whether or not a proper inspection has been performed (Step S233). For example, the determination unit 186 calculates a representative value of reliability of each position included in a region of interest or a general region. A representative value is the average, the median, the maximum, or the like of reliability of each position included in a region of interest or a general region. As long as a representative value is calculated on the basis of reliability of each position included in a region of interest or a general region, the representative value may be any value. The determination unit 186 compares the calculated value with a threshold value. For example, a method of setting a threshold value of reliability is similar to the method of setting a threshold value of an index.

When the representative value is greater than the threshold value in all the regions of interest, the determination unit 186 determines that a proper inspection has been performed. When there is a region of interest in which the representative value is not greater than the threshold value, the determination unit 186 determines that a proper inspection has not been performed.

A threshold value of reliability may be prepared for each region. For example, a threshold value of reliability of a region of interest may be 100% and a threshold value of reliability of a general region may be 80%. A threshold value of reliability of a region of interest and a threshold value of reliability of a general region may be the same. For example, a threshold value of reliability of all the regions may be 80%. A method of determining whether or not a proper inspection has been performed is not limited to the above-described method. As long as it is determined whether or not a proper inspection has been performed, any method may be used.

When the determination unit 186 determines that a proper inspection has been performed, the processing shown in FIG. 25 is completed. When the determination unit 186 determines that a proper inspection has not been performed, the determination unit 186 notifies the display control unit 182 of information of a region that should be inspected again. The representative value of reliability of the region is not greater than the threshold value. The display control unit 182 generates a graphic image signal for displaying second notification information that represents the region. Thereafter, the video signal processing circuit 12 combines the graphic image signal and a video signal and outputs the combined video signal to the display unit 5. The display unit 5 displays the second notification information on an inspection image. In this way, the display unit 5 notifies a user of the region that should be inspected again (Step S234). When Step S234 is executed, the processing shown in FIG. 25 is completed.

For example, a region that should be inspected again is displayed in a color different from that of a region for which a proper inspection has been performed. A region for which a proper inspection has not been performed may not be displayed and only a region that should be inspected again may be displayed. As long as a user can understand a region that should be inspected again, any display method may be used.

The display control unit 182 may display reliability on a 3D model in Step S232. The display control unit 182 may display second notification information on a 3D model in Step S234.

As described above, the determination unit 186 calculates reliability that represents the degree to which an imaging condition that has been set in a region of interest or a general region is satisfied in a determination step (Step S231). The display control unit 182 displays the reliability as observation information on the display unit 5 in an observation information display step (Step S232).

As described above, the determination unit 186 determines whether or not the imaging condition is satisfied by comparing the reliability with a threshold value in a determination step (Step S233). A method of operating an observation device according to each aspect of the present invention may include a second notification information display step. When the determination unit 186 determines that the imaging condition is not satisfied, the display control unit 182 displays second notification information that represents a region of interest or a general region including a position on a 3D model has not been observed on the display unit 5 in the second notification information display step (Step S234).

In the third embodiment, reliability is calculated and displayed. The reliability has any one of two or more values that represent the degree to which a region has been observed. For this reason, the endoscope device 1 can correctly notify a user of a region that has been thoroughly observed and a region that has not been thoroughly observed.

The endoscope device 1 automatically determines whether or not a proper inspection has been performed. In a case in which the endoscope device 1 determines that a proper inspection has been performed, a user can feel at ease and report completion of the inspection to a client, a supervisor, or the like. When the endoscope device 1 determines that a proper inspection has not been performed, the endoscope device 1 notifies a user of a region that should be inspected again. For this reason, a user can promptly start re-inspection.

While preferred embodiments of the invention have been described and shown above, it should be understood that these are examples of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of operating an observation device, the method comprising:
    an image display step;
    an estimation step;
    an identification step;
    a determination step; and
    an observation information display step,
    wherein the observation device includes:
        an insertion unit that includes an imaging device configured to acquire an image of a subject inside an observation object and is configured to be inserted into the observation object;
        a storage medium configured to store an imaging condition that has been set in each of a first region and a second region, the first region being part of a three-dimensional model of the subject, the second region being other than the first region in the three-dimensional model, the imaging condition of the first region and the imaging condition of the second region being different from each other; and
        a processor,
    the processor displays the image on a display in the image display step,
    the processor estimates, in the estimation step, a position of the imaging device and a posture of the imaging device, the position and the posture being a position and a posture, respectively, when the imaging device acquires the image,
    the processor identifies, in the identification step, a position on the three-dimensional model corresponding to a pixel of the image on the basis of the position and the posture that are estimated in the estimation step,
    the processor determines, in the determination step, whether or not the imaging condition that has been set in the first region or the second region including the position on the three-dimensional model is satisfied, and
    the processor displays, in the observation information display step, observation information on the display on the basis of a result of the determination step, the observation information representing whether or not the first region or the second region including the position on the three-dimensional model has been observed.

2. The method of operating the observation device according to claim 1, wherein the method further comprises an imaging condition setting step in which the processor sets the imaging condition to each of the first region and the second region.

3. The method of operating the observation device according to claim 1,
wherein the method further comprises a region setting step in which the processor sets the first region and the second region to the three-dimensional model.

4. The method of operating the observation device according to claim 3,
wherein the method further comprises:
a feature point detection step in which the processor detects a feature point in each of a plurality of images acquired by the imaging device;
an association step in which the processor associates the feature point between the images included in the plurality of images;
a calculation step in which the processor calculates a position of the imaging device and a posture of the imaging device on the basis of the feature point; and
a generation step in which the processor generates the three-dimensional model on the basis of the position and the posture calculated in the calculation step, and
before the region setting step is executed, the feature point detection step, the association step, the calculation step, and the generation step are executed.

5. The method of operating the observation device according to claim 2,
wherein input of the imaging condition from a user is not accepted in the imaging condition setting step.

6. The method of operating the observation device according to claim 3,
wherein input of information that represents the first region and the second region from a user is not accepted in the region setting step.

7. The method of operating the observation device according to claim 1,
wherein the processor estimates the position and the posture on the basis of at least the image and the three-dimensional model in the estimation step.

8. The method of operating the observation device according to claim 1,
wherein the processor estimates the position and the posture on the basis of only the image in the estimation step.

9. The method of operating the observation device according to claim 1,
wherein the storage medium is configured to store a non-observed position that is the position on the three-dimensional model for which it is determined that the imaging condition is not satisfied, and
the method further comprises a first notification information display step in which, when the non-observed position is behind a visual field of the imaging device, the processor displays first notification information that represents that there is the first region or the second region including the non-observed position on the display.

10. The method of operating the observation device according to claim 1,
wherein the imaging condition includes a plurality of conditions, and
the method further comprises a condition information display step in which, when the processor determines that at least one condition included in the plurality of conditions is not satisfied, the processor displays condition information that represents the at least one condition on the display.

11. The method of operating the observation device according to claim 1,
wherein the method further comprises a recording step in which, when the processor determines that the imaging condition that has been set to the first region is satisfied, the processor records the image in which a region corresponding to the first region is seen.

12. The method of operating the observation device according to claim 1,
wherein, when the processor determines that the imaging condition is satisfied, the processor displays, in the observation information display step, the observation information representing that the first region or the second region including the position on the three-dimensional model has been observed on the display.

13. The method of operating the observation device according to claim 1,
wherein, when the processor determines that the imaging condition is not satisfied, the processor displays, in the observation information display step, the observation information representing that the first region or the second region including the position on the three-dimensional model has not been observed on the display.

14. The method of operating the observation device according to claim 1,
wherein the processor calculates, in the determination step, an evaluation value that represents a degree to which the imaging condition that has been set in the first region or the second region is satisfied, and
the processor displays the evaluation value as the observation information on the display in the observation information display step.

15. The method of operating the observation device according to claim 14,
wherein the processor determines whether or not the imaging condition is satisfied by comparing the evaluation value with a threshold value in the determination step, and
the method further comprises a second notification information display step in which, when the processor determines that the imaging condition is not satisfied, the processor displays second notification information that represents the first region or the second region including the position on the three-dimensional model has not been observed on the display.

16. An observation device comprising:
an insertion unit that includes an imaging device configured to acquire an image of a subject inside an observation object and is configured to be inserted into the observation object;
a storage medium configured to store an imaging condition that has been set in each of a first region and a second region, the first region being part of a three-dimensional model of the subject, the second region being other than the first region in the three-dimensional model, the imaging condition of the first region and the imaging condition of the second region being different from each other; and
a processor,
wherein the processor is configured to display the image on a display,
the processor is configured to estimate a position of the imaging device and a posture of the imaging device, the position and the posture being a position and a posture, respectively, when the imaging device acquires the image, the processor is configured to identify a position on the three-dimensional model corresponding to a pixel of the image on the basis of the estimated position and posture, the processor is configured to determine whether or not the imaging condition that has been set in the first region or the second region including the position on the three-dimensional model is satisfied, and the processor is configured to display observation information on the display on the basis of a result of determination of the imaging condition, the observation information representing whether or not the first region or the second region including the position on the three-dimensional model has been observed.

17. A non-transitory computer-readable recording medium saving a program for causing a computer of an observation device to execute:
    an image display step;
    an estimation step;
    an identification step;
    a determination step; and
    an observation information display step,
    wherein the observation device includes:
        an insertion unit that includes an imaging device configured to acquire an image of a subject inside an observation object and is configured to be inserted into the observation object; and
        a storage medium configured to store an imaging condition that has been set in each of a first region and a second region, the first region being part of a three-dimensional model of the subject, the second region being other than the first region in the three-dimensional model, the imaging condition of the first region and the imaging condition of the second region being different from each other,
    the computer displays the image on a display in the image display step,
    the computer estimates, in the estimation step, a position of the imaging device and a posture of the imaging device, the position and the posture being a position and a posture, respectively, when the imaging device acquires the image,
    the computer identifies, in the identification step, a position on the three-dimensional model corresponding to a pixel of the image on the basis of the position and the posture that are estimated in the estimation step,
    the computer determines, in the determination step, whether or not the imaging condition that has been set in the first region or the second region including the position on the three-dimensional model is satisfied, and
    the computer displays, in the observation information display step, observation information on the display on the basis of a result of the determination step, the observation information representing whether or not the first region or the second region including the position on the three-dimensional model has been observed.

18. The non-transitory computer-readable recording medium according to claim 17,
    wherein the program causes the computer to further execute a region setting step in which the computer sets the first region and the second region to the three-dimensional model.

19. The non-transitory computer-readable recording medium according to claim 17,
    wherein the program causes the computer to further execute:
        a feature point detection step in which the computer detects a feature point in each of a plurality of images acquired by the imaging device;
        an association step in which the computer associates the feature point between the images included in the plurality of images;
        a calculation step in which the computer calculates a position of the imaging device and a posture of the imaging device on the basis of the feature point; and
        a generation step in which the computer generates the three-dimensional model on the basis of the position and the posture calculated in the calculation step, and
    before the region setting step is executed, the feature point detection step, the association step, the calculation step, and the generation step are executed.

20. The non-transitory computer-readable recording medium according to claim 17,
    wherein the computer estimates the position and the posture on the basis of at least the image and the three-dimensional model in the estimation step.

* * * * *